US008986607B2

(12) United States Patent
Anderle et al.

(10) Patent No.: US 8,986,607 B2
(45) Date of Patent: *Mar. 24, 2015

(54) METHOD FOR THE VALIDATABLE INACTIVATION OF PATHOGENS IN A BIOLOGICAL FLUID BY IRRADIATION

(75) Inventors: Heinz Anderle, Klosterneuburg (AT); Peter Matthiessen, Vienna (AT); Hans-Peter Schwarz, Vienna (AT); Peter Turecek, Klosterneuburg (AT); Thomas Kreil, Klosterneuburg (AT); Daniel R. Boggs, Libertyville, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 1239 days.

This patent is subject to a terminal disclaimer.

(21) Appl. No.: 10/547,172

(22) PCT Filed: Feb. 27, 2004

(86) PCT No.: PCT/EP2004/001994
§ 371 (c)(1),
(2), (4) Date: May 22, 2006

(87) PCT Pub. No.: WO2004/075931
PCT Pub. Date: Sep. 10, 2004

(65) Prior Publication Data
US 2006/0257877 A1 Nov. 16, 2006

Related U.S. Application Data

(60) Provisional application No. 60/449,852, filed on Feb. 27, 2003.

(51) Int. Cl.
*A61L 2/00* (2006.01)
*C12N 13/00* (2006.01)
*G01J 1/08* (2006.01)
*A61L 2/10* (2006.01)
*A61L 2/28* (2006.01)
*G01J 1/42* (2006.01)
*G01J 1/48* (2006.01)
*A61M 1/36* (2006.01)
*C02F 1/32* (2006.01)

(52) U.S. Cl.
CPC ............... *G01J 1/08* (2013.01); *A61L 2/0011* (2013.01); *A61L 2/0017* (2013.01); *A61L 2/0052* (2013.01); *A61L 2/10* (2013.01); *A61L 2/28* (2013.01); *G01J 1/42* (2013.01); *G01J 1/48* (2013.01); *A61L 2202/22* (2013.01); *A61M 1/3681* (2013.01); *C02F 1/32* (2013.01); *C02F 2201/326* (2013.01)
USPC .............................. 422/22; 435/173.1; 422/24

(58) Field of Classification Search
None
See application file for complete search history.

(56) References Cited

U.S. PATENT DOCUMENTS

| 4,481,189 | A | 11/1984 | Prince |
| 4,540,573 | A | 9/1985 | Neurath et al. |
| 4,613,501 | A | 9/1986 | Horowitz |
| 4,730,922 | A | 3/1988 | Bach et al. |
| 4,946,648 | A | 8/1990 | Dichtelmüller et al. |
| 5,133,932 | A | 7/1992 | Gunn et al. |
| 5,480,562 | A | 1/1996 | Lemelson |
| 5,567,616 | A | 10/1996 | Dill, II |
| 5,744,094 | A | 4/1998 | Castberg et al. |
| 5,919,907 | A * | 7/1999 | Shanbrom ............... 530/362 |
| 6,190,608 | B1 | 2/2001 | Laub et al. |
| 6,329,136 | B1 | 12/2001 | Lagunas-Solar et al. |
| 6,468,433 | B1 | 10/2002 | Tribelski |
| 6,540,967 | B2 | 4/2003 | Mausbach et al. |
| 6,576,201 | B1 | 6/2003 | Woo et al. |
| 6,586,172 | B1 | 7/2003 | Gunn et al. |
| 6,596,542 | B1 | 7/2003 | Schulz |
| 2003/0049809 | A1 | 3/2003 | Kaiser et al. |
| 2003/0147770 | A1 | 8/2003 | Brown et al. |

FOREIGN PATENT DOCUMENTS

| DE | 1 269 389 | | 5/1968 | |
| DE | 19957997 A1 | | 6/2001 | |
| EP | 0 607 941 A2 | | 7/1994 | |
| GB | 000781.0 | * | 4/2000 | ........... A61L 2/00 |
| GB | WO 01/74407 | * | 10/2001 | ........... A61L 2/00 |
| JP | 7-196531 | | 8/1995 | |
| JP | 11-286453 | | 10/1999 | |
| WO | WO94/28210 A1 | | 12/1994 | |

(Continued)

OTHER PUBLICATIONS

Mark et al. "The photolysis of potassium peroxodisulphate in aqueous solution in the presence of tert-butanol: a simple actinometer for 254 nm radiation" J. Photochemiistry and Photobiology A: Chemistry, vol. 55 (2), Dec. 1990, Abstract Only.*
Joseph J. Jankowski, David J. Kieber and Kenneth Mopper "Nitrate and Nitrite Ultraviolet Actinometers" Photochemistry and Photobiology, 1999, 70(3): 319-328.*
Adhikari, C., et al; *2002 Annual Meeting and Food Expo*—Anaheim, California; "Chemical Actinometry in UV Treated Juices"; Session 91E on Jun. 18, 2002; 1 page (2002).
Alfano, O.M., et al; *Chemical Engineering Science*; Review Article No. 18; "Radiation Field Modelling in Photoreactors—Homogeneous Media"; vol. 41:3; pp. 421-444 (1986).
Allan, W., et al; *Photodermatology, Photoimmunology & Photomedicine*; "A Device for Minimizing the Risk of Overexposure of Patients Undergoing Phototherapy"; vol. 18; pp. 199-201 (2002).
Benesi, E.; *General Motors Engineering Journal*; "Design of a Centrifugal Filmer for the Ultraviolet Irradiation of Liquids"; pp. 1-8 (1956).

(Continued)

*Primary Examiner* — Thane Underdahl
(74) *Attorney, Agent, or Firm* — Morgan, Lewis & Bockius LLP

(57) ABSTRACT

A validatable method for determining a photochemically effective dose for inactivating pathogens in a fluid sample is described herein. In particular, the instant invention covers methods for determining a photochemically effective dose sufficient to inactivate pathogens in a biological sample while leaving biologically active substances of interest unaffected. A batch irradiation reactor effective for inactivating pathogens in biological samples is also described.

30 Claims, 10 Drawing Sheets

(56) References Cited

FOREIGN PATENT DOCUMENTS

| WO | WO96/02571 A1 | 2/1996 | | |
|---|---|---|---|---|
| WO | WO97/03706 A1 | 2/1997 | | |
| WO | WO 97/33629 | * | 9/1997 | ............... A61L 2/20 |
| WO | WO97/33629 A1 | 9/1997 | | |
| WO | WO00/03750 A1 | 1/2000 | | |
| WO | WO00/20045 A1 | 4/2000 | | |
| WO | WO00/25581 A1 | 5/2000 | | |
| WO | WO 00/62025 | 10/2000 | | |
| WO | WO01/54738 A1 | 8/2001 | | |
| WO | WO01/74407 A1 | 10/2001 | | |
| WO | WO 02/068917 A2 | 9/2002 | | |
| WO | WO 02/068917 A3 | 9/2002 | | |
| WO | WO03/007998 A1 | 1/2003 | | |
| WO | WO2004/075931 A3 | 9/2004 | | |

OTHER PUBLICATIONS

Bolton, J.R., et al; *Journal of Environmental Engineering*; "Standardization of Methods for Fluence (UV Dose) Determination in Bench-Scale UV Experiments"; pp. 209-215 (2003).

Bolton, J.R.; *EPA Newsletter*; "Light Compendium—Ultraviolet Principles and Applications"; No. 66; pp. 9-36 (1999).

Bowen, E.J.; *The Chemical Aspects of Light*; Second Revised Edition; Oxford at Clarendon Press; Appendix IV; pp. 282-283 (1949).

Braslavsky, S.E., et al; *Glossary of Terms Used in Photochemistry*; International Union of Pure and Applied Chemistry; $2^{nd}$ Edition; pp. 1-73 (1996).

Brauer, H.D., et al; *Photochemistry and Photobiology*; "A New Reusable Chemical Actinometer for UV Irradiation in the 248-334nm Range"; vol. 37:5; pp. 587-599 (1983).

Brummelhuis, H.G.J.; *Methods of Plasma Protein Fractionation*; Ed. J.M. Curling; Academic Press; "Preparation of the Prothrombin Complex"; pp. 117-128 (1980).

Budowsky, E.I., et al; *Archives of Virology*; "Principles of Selective Inactivation of Viral Genome"; vol. 68; pp. 249-256 (1981).

Cabaj, A., et al; *Radiation Protection Dosimetry*; "Measurement of Ultraviolet Radiation with Biological Dosemeters"; vol. 91:1-3; pp. 139-142 (2000).

Cabaj, A., et al; *Wat. Res.*; "Biodosimetry: Model Calculations for U.V. Water Disinfection Devices"; vol. 30:4; pp. 1003-1009 (1996).

Calvert, J.G., et al; *Journal of the American Chemical Society*; "Precision Actinometry at Low Light Intensities with Malachite Green Leucocyanide"; vol. 74; pp. 2101-2103 (1952).

Chin, S., et al; *Blood*; "Virucidal Short Wavelength Ultraviolet Light Treatment of Plasma and Factor VIII Concentrate: Protection of Proteins by Antioxidants"; vol. 86:11; pp. 4331-4336 (1995).

Chin, S., et al; *Photochemistry and Photobiology*; "Virucidal Treatment of Blood Protein Products with UVC Radiation"; vol. 65:3; pp. 432-435 (1997).

Dainton, F.S., et al; *Nature*; "Use of Nitrous Oxide to Discriminate between Various Forms of Hydrogen Atoms Existing in Aqueous Solutions of Potassium Iodide Irradiated with Ultra-Violet Light"; No. 4728; p. 879 (1960).

Dichtelmueller, H., et al; *Immun. Infekt.*; "Monitoring of Sterilization Procedures for Plasma Derivatives Using Bacteriophages"; vol. 16; pp. 18-20 (1988). [See English Language Summary].

Favaro, G.; *Photochemistry and Photostability*; "Actinometry: Concepts and Experiments"; vol. 225; pp. 295-304 (1998).

Fisher, G.J., et al; *Photochemistry and Photobiology*; "A Calorimetric Determination of the Quantum Yield for the Ionization of Malachite Green Cyanide by Ultraviolet Radiation"; vol. 6; pp. 757-767 (1967).

Forney, L.J., et al; *AIChE Journal*; "Optimum Photolysis in Taylor-Couette Flow"; vol. 49:3; pp. 727-733 (2003).

Gauglitz, G., et al; *Journal of Photochemistry*; "Chemical Actinometry in the UV by Azobenzene in Concentrated Solution: A Convenient Method"; vol. 30; pp. 121-125 (1985).

Gauglitz, G., et al; *Journal of Photochemistry*; "Azobenzene as a Convenient Actinometer: Evaluation Values for UV Mercury Lines and for the $N_2$ Laser Line"; vol. 15; pp. 255-257 (1981).

Gauglitz, G., et al; *Zeitschrift fuer Physikalische Chemie*; "Photokinetische Grundlagen Moderner Chemischer Aktinometer"; vol. 139; pp. 237-246 (1984). [See English Language Summary].

Gauglitz, G.; *EPA Newsletter*; "Modern Chemical Actinometry"; pp. 49-53 (1983).

Habel, K., et al; *Journal of Immunology*; "A Continuous Flow Method of Exposing Antigens to Ultraviolet Radiation"; vol. 56; pp. 273-279 (1946).

Harris, R.E., et al; *Applied Microbiology*; "Stability of Minute Virus of Mice to Chemical and Physical Agents"; vol. 28:3; pp. 351-354 (1974).

Hart, H., et al; *Vox Sang*; "Inactivation of Viruses During Ultraviolet Light Treatment of Human Intravenous Immunoglobulin and Albumin" vol. 64; pp. 82-88 (1993).

Heidt, L.J., et al; *Journal of the American Chemical Society*; "Influence of Several Variables Encountered in Photochemical Work upon the Intensity of Light . . . "; vol. 73; pp. 5728-5731 (1951).

Heinrich, D., et al; *Thrombosis Research*; "Clinical Evaluation of the Hepatitis Safety of a β- Propiolactone/Ultraviolet Treated Factor IX Concentrate (PPSB)"; vol. 28; pp. 75-83 (1982).

Kirk, A.D., et al; *Anal. Chem.*; "Errors in Ferrioxalate Actinometry"; vol. 55; pp. 2428-2429 (1983).

Koutchma, T., et al; *IUVA News*; "Effectiveness of UV Disinfection of Juice"; vol. 4:5; pp. 21-23 (2002).

Kuhn, H.J., et al; *Pure & Appl. Chem.*; "Chemical Actinometry"; vol. 61:2; pp. 187-210 (1989).

Kurth, J., et al; *Development in Biological Standardization*; "Efficient Inactivation of Viruses and Mycoplasma in Animal Sera Using UVC Irradiation"; vol. 99; pp. 111-118 (1999).

Marx, G, et al; *Photochemistry and Photobiology*; "Protecting Fibrinogen with Rutin During UVC Irradiation for Viral Inactivation"; vol. 63:4; pp. 541-546 (1996).

McLean, I.W., et al; *Progress in Medical Virology*; "Experiences in the Production of Poliovirus Vaccines"; vol. 1; pp. 122-164 (1958).

Moroson, H., et al; *Nature*; "A Sensitive Chemical Actinometer for Ultra-Violet Radiation"; vol. 204; pp. 676-678 (1964).

Morowitz, H.J.; *Science*; "Absorption Effects in Volume Irradiation of Microorganisms"; vol. 111; pp. 229-230 (1950).

Oliphant, J.W., et al; *Public Health Reports*; "Homologous Serum Jaundice"; vol. 61:17; pp. 598-602 (1946).

Oppenheimer, F., et al; *American Journal of Public Health*; "The Ultraviolet Irradiation of Biological Fluids in Thin-Flowing Films"; vol. 49:7; pp. 903-923 (1959).

Prodouz, K.N., et al; *Blood*; "Use of Laser-UV for Inactivation of Virus in Blood Products"; vol. 70:2; pp. 589-592 (1987).

Qualls, R.G., et al; *Applied and Environmental Microbiology*; "Bioassay and Dose Measurement in UV Disinfection"; vol. 45:3; pp. 872-877 (1983).

Rahn, R.O., et al; *Photochemistry and Photobiology*; "Quantum Yield of the Iodide-Iodate Chemical Actinometer: Dependence on Wavelength and Concentration"; vol. 78:2; pp. 146-152 (2003).

Rahn, R.O., et al; *Photochemistry and Photobiology*; "Dosimetry of Room-Air Germicidal (254 nm) Radiation Using Spherical Actinometry"; vol. 70:3; pp. 314-318 (1999).

Rahn, R.O.; *Photochemistry and Photobiology*; "Use of Potassium Iodide as a Chemical Actinometer"; vol. 58:6; pp. 874-880 (1993).

Rahn, R.O.; *Photochemistry and Photobiology*; "Potassium Iodide as a Chemical Actinometer for 254 nm Radiation: Use of Iodate as an Electron Scavenger"; vol. 66:4; pp. 450-455 (1997).

Rideal, E.K., et al; *Proceedings of the Royal Society*; "The Photochemistry of Native Proteins"; Series A; vol. 205; pp. 391-408 (1951).

Rommelaere, J., et al; *Photochemistry and Photobiology*; "UV-Enhanced Reactivation of Minute-Virus-of-Mice: Stimulation of a Late Step in the Viral Life Cycle"; vol. 33; pp. 845-854 (1981).

Schenck, H.U., et al; *Journal of Pharmaceutical Sciences*; "Structure of Polyvinylpyrrolidone-Iodine (Povidone-Iodine)"; vol. 68:12; pp. 1505-1509 (1979).

Schulz, C.R., et al; *Conference Proceedings of the International Ultraviolet Association's $1^{st}$ International Congress on Ultraviolet Technologies*, Jun. 15-16, 2001; "Development of a Flow-Through Chemical Actinometer System for Measuring Irradiance in UV Reactors"; 1 page (2001).

(56) References Cited

OTHER PUBLICATIONS

Sczechowski, J.G., et al; *Chemical Engineering Science*; "A Taylor Vortex Reactor for Heterogeneous Photocatalysis"; vol. 50:20; pp. 3163-3173 (1995).
Stephan, W., et al; *Thrombos. Haemostas.*; "Long-Term Tolerance and Recovery of β-Propiolactone/Ultraviolet (βPL/UV) Treated PPSB in Chimpanzees"; vol. 46:2; pp. 511-514 (1981).
Taylor, A.R.; *Annals New York Academy of Sciences*; "Effects of Nonionizing Radiations on Animal Viruses"; vol. 83; pp. 670-683 (1960).
Taylor, A.R., et al; *Journal of Immunology*; "Inactivation of Poliomyelitis Virus for the Preparation of Vaccines"; vol. 79; pp. 265-275 (1957).
Vincze, L., et al; *Journal of Photochemistry and Photobiology A: Chemistry*; "Flow Actinometry in a Thin Film Reactor: Modeling and Measurements"; vol. 123; pp. 7-13 (1999).
Von Sonntag J.; *Journal of Photochemistry and Photobiology A: Chemistry*; "The Influence of Solute Absorbance in Laser Flash Photolysis—Actinometry in Experiment and Theory at Non-Vanishing Absorbance"; vol. 126; pp. 1-5 (1999).
Wright, H.B., et al; *Trojan Technologies, Inc.,*; "UV Dose Required to Achieve Incremental Log Inactivation of Bacteria, Viruses, and Protozoa"; Revision Sep. 12, 2001; 5 pages (2001).
Yokota, T., et al; *Journal of Chemical Engineering of Japan*; "Estimation of Light Absorption Rate in a Tank Type Photoreactor with Multiple Lamps Inside"; vol. 28:3; pp. 300-305 (1995).
Casillas, G. et al., "Polyvinylpyrrolidone (PVP): A New Precipitating Agent for Human and Bovine Factor VIII and Fibrinogen," *British Journal of Haematology*, 1982, vol. 50, pp. 665-672.
Fraenkel-Conrat, H., "The Reaction of Tobacco Mosaic Virus With Iodine," *The Journal of Biological Chemistry*, Nov. 1955, vol. 217, No. 1, pp. 373-381.
Harington, C.R. et al., "Electrometric Titration of Insulin. Preparation and Properties of Iodinated Insulin," *Biochem J.*, May 1936, vol. 30, No. 5, pp. 809-820.
Hughes, W.L., Jr. et al., "Preparation and Properties of Serum and Plasma Proteins. XXIV. Iodination of Human Serum Albumin," *The Journal of the American Chemical Society*, 1950, vol. 72, pp. 452-457.
Anderle, H. et al., "Assessment of the Efficacy of Virus Inactivation by UV-C Treatment of Therapeutic Proteins," $2^{nd}$ International Congress on Ultraviolet Technologies, Vienna, Jul. 9-11, 2003, 5 pages.
Demas, J.N. et al., "Determination of the Quantum Yield of the Ferrioxalate Actinometer with Electrically Calibrated Radiometers," *The Journal of Physical Chemistry*, 1981, vol. 85, No. 19, pp. 2766-2771.
Harm, W. "Inactivation of cells and viruses," Chapter 4 in *Biological effects of ultraviolet radiation*, 1980, Press Syndicate of the University of Cambridge: New York, NY, 25 pages.
Sommer, R. et al., "Inactivation of Bacteriophages in Water by Means of Non-Ionizing (UV-253.7 nm) and Ionizing (Gamma) Radiation: A Comparative Approach," *Wat. Res.*, 2001, vol. 35, No. 13, pp. 3109-3116.
Yarus, M. et al., "Ultraviolet Sensitivity of the Biological Activity of ΦX174 Virus, Single-Stranded DNA, and RF DNA," *Biophysical Journal*, 1967, vol. 7, pp. 267-278.

Asahina et al., "Effect of Medium Pressure and Low Pressure Ultraviolet Systems on the Inactivation of Selected Bacteriophages"; *Proceedings of the "Disinfection 2002" conference*, Alexandria, VA: Water Environment Federation, (2002), 10 pgs.
Battigelli et al., "The Inactivation of Hepatitis a Virus and Other Model Viruses by UV Irradiation"; *Water. Sci. Tech.*, vol. 27, No. 3-4, pp. 339-342 (1993).
Bering et al., "Methoden zur Messung der Wirksamkeit violetter und ultravioletter Strahlequellen"; *Strahlentherapie*, pp. 189-207 (1912).
Bolton J., "Ultraviolet Principles and Applications," *European Photochemical Association Newsletter*, 66:9-36, 1999.
Cortelyou et al., "Effects of Ultraviolet Irradiation on Large Populations of Certain Water-Borne Bacteria in Motion. I. The Development of Adequate Agitation to Provide an Effective Exposure Period", *Appl. Environ. Microbiol.*, V. 2, pp. 227-235 (1954).
Cortelyou et al., "Effects of Ultraviolet Irradiation on Large Populations of Certain Water-Borne Bacteria in Motion. II. Some Physical Factors Affecting the Effectiveness of Germicidal Ultraviolet Irradiation", *Appl. Environ. Microbiol.*, V. 2, pp. 269-273 (1954).
Hackradt A., "Uber die kolorimetrische Ausdosierung kunstlicher Lichtquellen auf Grund der Zersetzung einer Jodwasserstofflosung", *Strahlentherapie*, V. 12, pp. 843-845 (1922).
Hatchard et al., "A New Sensitive Chemical Actinometer. II. Potassium Ferrioxalate as a Standard Chemical Actinometer", Proceedings of the Royal Society of London A, pp. 518-536 (1956).
Hosseini et al; "Inactivating Advetitious Viruses While Preserving Biological Activity", *BioPharm International*, Dec. 2002, pp. 35-40 (2002).
Jankowski et al., "Development and Intercalibration of Ultrasviolet Solar Actinometers", *Photochemistry and Photobiology*, vol. 71(4), pp. 431-440 (2000).
Jankowski et al., "Nitrate and Nitrite Ultraviolet Actinometers", *Photochemistry and Photobiology*, vol. 70(3), pp. 319-328 (1999).
Latarjet et al., "Precisions sur L'inactivation des Bacteriophages par les Rayons Ultraviolets", *Annales de l'Institut Pasteur*, V. 71, pp. 336-339 (1945).
Mark, et al., "The Photolysis of Potassium Peroxodisulphate in Aqueous Solution in the Presence of *Tert*-butanol: a Simple Actinometer for 254 nm Radiation", *Journal of Photochemistry and Photobiology*, vol. 55, pp. 157-168 (1990).
Murray et al., "Effect of Ultraviolet Radiation on the Infectivity of Icterogenic Plasma", *Journal of the American Medical Association*, vol. 157 (1), pp. 8-14, (1955).
Rivers et al., "Ultra-Violet Light and Vaccine Virus. II. The Effect of Monochromatic Ultra-Violet Light upon Vaccine Virus." Journal of Experimental Medicine, vol. 47, pp. 45-49, (1928).
Forney L. J. et al., "Ultraviolet Disinfection: Similitude in Taylor-Couette and Channel Flow," *Environmental Science and Technology*, vol. 37, No. 21, Nov. 1, 2003, pp. 5015-5020.
Koutchma T. et al., "Ultraviolet disinfection of juice products in laminar and turbulent flow reactors," *Innovative Food Science and Emerging Technologies*, vol. 5, No. 2, Jun. 2004, pp. 179-189.
Leuker G., "Dexcription and application of biodosimetry—A testing procedure for UV systems," *AQUA*, vol. 48, No. 4, 1999, pp. 154-160.
European Search Report, Appln. No. EP 10009727.8-2113, Publ. No. EP2266630 (A1), Publ. Date: Dec. 29, 2010, 3 pgs.
European Search Report, Appln. No. EP 10008758.4-2113, Publ. No. EP1784229, Publ. Date Mar. 2, 2006, 4 pgs.

\* cited by examiner

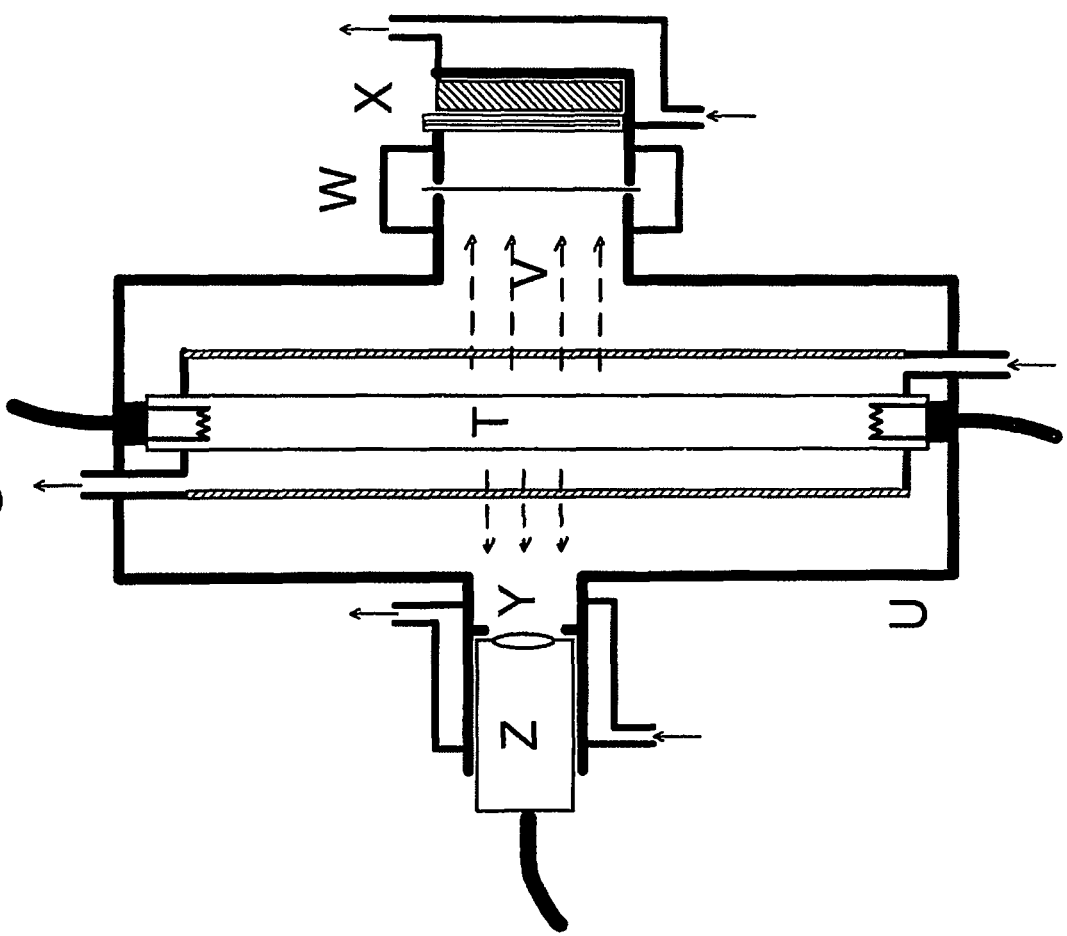

METHOD FOR THE VALIDATABLE INACTIVATION OF PATHOGENS IN A BIOLOGICAL FLUID BY IRRADIATION

CROSS REFERENCE TO RELATED APPLICATIONS

The present application is a U.S. National Phase of International Patent Application No. PCT/EP2004/001994, filed Feb. 27, 2004, which claims the benefit of U.S. Provisional Application No. 60/449,852, filed Feb. 27, 2003, the contents of which are expressly incorporated herein by reference in their entireties for all purposes.

FIELD OF THE INVENTION

The present invention relates to a method and apparatus for photochemical pathogen inactivation by batch irradiation, which prior to the present invention was considered too complex and unworkable. In particular, the invention advantageously permits those skilled in the art to determine an effective light dose for photochemical pathogen inactivation.

BACKGROUND OF THE INVENTION

Treatment of blood, blood cells, plasma, serum, plasma fractions, other biological fluids and protein solutions by irradiation has been a widely investigated approach to inactivate pathogenic viruses, in particular, small single-stranded non-enveloped DNA viruses. Examples of irradiation treatment currently under study include short-wave ultraviolet light, long-wave ultraviolet light, visible light with photosensitizing compounds, and broad-spectrum high-intensity flash light.

In the 1930's, small volumes of autologous whole blood were exposed to UV irradiation from a medium-pressure mercury vapor lamp to inactivate infectious organisms. By re-infusion of the irradiated blood, an apparent immunostimulatory effect was observed.

Between 1946 and 1955, treatment of pooled plasma with UV-C light to inactivate infectious agents had been investigated in the United States. The first encouraging results lead to UV-C treatment at 253.7 nm as a minimum requirement for therapeutically applicable human plasma (Murray et al. 1955). With the introduction of electronic spectrophotometry, plasma as well as virus culture solutions containing plasma or serum were determined to be optically opaque to 253.7 nm-light with a penetration depth of less than 1 mm (Suhrmann and Kollath 1928). Therefore, various thin-film irradiators were constructed for large-volume plasma sterilization or vaccine attenuation. Examples include the Habel-Sockrider irradiator (Habel and Sockrider 1947), the Milzer-Oppenheimer-Levinson centrifugal film generating device with water-cooled lamps (Milzer et al. 1945; Benesi 1956; Taylor et al. 1957a; Taylor et al. 1957b; McLean and Taylor 1958; Oppenheimer et al. 1959), and the Dill irradiator (Murray et al. 1955) (Dill Instruments Co.), which is the only design still commercially available.

Despite the foregoing advances, serum hepatitis persisted (Neefe 1949; Barnett et al. 1950; James et al. 1950). Exhaustive studies determined that UV doses required to inactivate Hepatitis B virus severely reduced biological activity of plasma proteins, and that method was abandoned in the late 1950's (Murray et al. 1955; Kallenbach et al. 1989). In 1958, an improved combination administration of beta-propiolactone and subsequent UV-C irradiation was introduced. This process was able to inactivate serum hepatitis viruses but leave intact at least those biological activities of prothrombin complex, immunoglobulins, and albumin (Smolens and Stokes 1954; Hartman et al. 1955; Prince et al. 1983). From 1968 onwards, this process was applied by commercial plasma fractionators in manufacturing of combined albumin-immunoglobulin serum concentrate, and from 1976 onwards, of a prothrombin complex concentrate with use of a Dill thin-film UV irradiator (Stephan et al. 1981, Stephan 1982a, 1982b). Infectivity studies in chimpanzees and later in cell cultures showed an effective inactivation of hepatitis A, B and C (Heinrich et al. 1982, 1987, Frösner et al. 1983, Prince et al. 1983, 1984, Stephan 1989), while HIV proved to be more resistant against UV-C (Dichtelmüller et al. 1987, 1993). The apparent insufficiency of the beta-propiolactone/UV-C treatment to inactivate the AIDS virus HIV in a prothrombin complex concentrate (Kleim et al. 1990, Kupfer et al. 1995) and the availability of other physical and physicochemical inactivation methods, such as heat or detergent treatment, led to the abandonment of the beta-propiolactone-UV-C method in 1990 (Pustoslemsek et al. 1993).

In the 1980's, Dichtelmüller et al. (1987) and Kallenbach et al. (1989) confirmed that UV-C alone would require excessively high doses to inactivate HIV in blood plasma, and UV-B was ineffective for pathogen inactivation (Prodouz et al. 1987).

On the other hand, small non-enveloped DNA viruses that are insufficiently susceptible to physical and physicochemical inactivation methods, are effectively inactivated by UVC light. A paradigm is the family of parvoviruses, such as Kilham Rat Virus (Proctor et al. 1972), Murine Minute Virus (MMV) (Harris et al. 1974, Rommelaere et al. 1981), and Porcine Parvovirus (PPV) (Brown 1981). For example, U.S. Pat. No. 6,190,608 describes a UV-C 253.7 nm fluence (the irradiant energy incident at the sample distance divided per area, expressed as $erg/mm^2$, $mJ/cm^2$ or $J/m^2$) of 12 $mJ/cm^2$ inactivated MMV in a solution containing 2 mg immunoglobulins/mL.

In addition, a fluence of 9-25 $mJ/cm^2$ is sufficient to inactivate parvoviruses in a concentrated solution of fibrinogen (WO 96/02571) or a dilute solution of purified coagulation factors (JP patent publ. 196531/1995). Higher UV dose of 100 $mJ/cm^2$ have been reported for the necessary minimum for plasma (Chin et al. 1995), fibrinogen (Marx et al, 1996), albumin, immunoglobulins (Hart et al. 1993; Chin et al. 1997), and animal sera (Kurth et al. 1999), although fluences as low as 50 $mJ/cm^2$ effectively inactivate parvoviruses (Chin et al. 1997).

Other examples for treating biological samples, such as plasma and red blood cells, include generation of singlet oxygen by a photosensitizer and light, or by flash-photolysis effects of high-intensity, broad-spectrum light flashes from a Xe tube. The technical advances in electronic light measurement and the availability of digital radiometers facilitated determination of irradiance from a light source, so that fluence data are routinely determined and disclosed.

Plasma proteins have demonstrated a high sensitivity to UV or photosensitized irradiation. The alteration of UV-C-irradiated plasma and plasma proteins resulted in prolonged coagulation time (Cutler et al. 1950; Cutler et al. 1955), changed electrophoretic mobility (Hellbrügge and Marx 1952; Larin 1958), aggregation (Engelhard and Eikenberg 1955), alteration of sedimentation properties in the ultracentrifuge (Claesson 1956), and antibody titer reduction (Battisto et al. 1953; Kleczowski 1954). For example, UV-C treated fibrinogen shows decreased clot elasticity (Di Benedetto et al. 1963a, 1963b, 1963c) and delayed clotting at >100 $mJ/cm^2$ (Marx et al. 1996); factor VIII activity is reduced in UV-C treated plasma (Kallenbach et al. 1989; Chin et al. 1995); fibrinogen clotting time is markedly increased, and von Willebrand factor and factor VIII activity is slightly decreased in methylene-blue/light treated fresh frozen plasma (Aznar et al. 1999).

To minimize the deleterious effect of ionizing and UVC radiation on proteins, quenchers of radical oxygen species have been used, in particular the flavonoid rutin (Erdmann 1956, WO94/28210), ascorbic acid (Erdmann 1956), and creatinine (JP 11286453-A) as an UV-C absorbing additive. However, if these additives supplement an additional absorbance at the wavelength used, too little UV-C energy may actually reach the pathogens. However, an excess of applied energy readily damages the proteins, and it is therefore necessary to not exceed the UV or visible light dose required for sufficient pathogen inactivation, and to calculate or determine this dose as accurately as possible.

Another possibility to protect proteins from singlet oxygen, which is generated from dissolved atmospheric oxygen by photoenergetically excited substances such as tryptophan derivatives present in the solution, is to remove the oxygen dissolved in the solution before the irradiation, and to replace the oxygen by an inert gas atmosphere, e.g. by nitrogen flushing, during the irradiation (Henzler and Kaiser 1998).

In relation to the above, electronic radiometers and spectroradiometers are used to measure radiant energy from a light source ($J/m^2$, $mJ/cm^2$) and radiance ($W/m^2$, $mW/cm^2$), or the incident light energy or power termed irradiant energy and irradiance. Such radiometer sensors are usually made of photovoltaic or photoelectric materials, such as semiconductor photocells or photodiodes optionally coated with a luminescence-doped phosphor layer to convert ultraviolet into visible radiation (Latarjet et al. 1953). One main application of radiometer sensors is to monitor light sources. Radiometer sensors have found widespread use in water disinfection and in phototherapy. The spatial response of such sensors is critical for an accurate irradiant power determination e.g. in UV-A and UVB therapy cabinets (Pye and Martin 2000, Martin and Pye 2000). To apply the accurate light dose, these devices have to be validated and calibrated by radiometry (Taylor et al. 2002), but the problem of the intensity decline by lamp aging has been settled only recently by the use of a radiometric target sum dose which has to be attained (Allen and Diffey 2002). A similar approach to compensate protein irradiation experiments for variations in lamp intensity was the use of a radiometric lamp monitor with an integrating counter (Rideal and Roberts 1951).

Electronic sensors mounted at the end of the light path (Taylor et al. 1941) are only of limited use in the irradiation of absorbing biological fluids, and the use of radiometer sensor measurements or signals to determine a or calculate a fluence (dose) or fluence rate (dose rate) distribution in a photochemical or pathogen photoinactivation reactor is limited by the laws of optics. A point source such as a bulb obeys the inverse square law in all directions, while a tubular source such as a fluorescent tube does not. It would in theory be possible to calculate a light energy distribution in an irradiated target only if specific properties were known: reflecting and scattering properties of surfaces; refractive properties of materials; absorption properties of passed and irradiated media. However, models have only been established for very simple systems, such as tubular cells or the elliptical photoreactor (Alfano et al. 1986a, 1986b).

Chemical actinometry measures the effect of light on a photochemical reactant mixture (Kuhn et al. 1989; Favaro 1998). In general, established photochemical actinometers with known quantum yield and temperature dependence can surpass electronic devices in reproducibility and stability. Photochemical reaction products should be measured on-line most conveniently e.g. by spectrophotometry or chemical sensors (Gauglitz 1983). The photochemical approach has therefore found general acceptance to determine both a light source's fluence rate or irradiant power.

A preferred approach employs total opacity of the actinometric solution at the measured wavelength, so that the photochemical reaction occurs only at the very surface (Kuhn et al. 1989; Favaro 1998). Therefore sufficiently high reactant concentrations are preferred.

For UV-C measurement, the classical actinometers are uranyl oxalate (Bowen 1949, Kuhn et al. 1989) and the ferrioxalate actinometer, but use of the first is limited by the Uranium radiotoxicity, and of the latter by UV-B, UV-A, and visible light sensitivity (Kirk and Namasivayam, 1983). Hydrogen sulfite or hydrogen cyanide adducts of triphenylmethane dyes also are as well known as UV-C-sensitive actinometers. For example, the colorless malachite green leucocyanide dissolved in ethanol does not show a long-wave UV or visible light sensitivity, but the green photoproduct absorbs additionally in the UV-C range (Calvert and Rechen 1952, Fisher et al. 1967). Azobenzene (Actinochrome 2R 245/440) in methanol enables a reuse of the actinometric solution (Gauglitz and Hubig 1981, 1984, 1985) as well as heterocoerdianthrone endoperoxide (Actinochrome 1R 248/334) (Brauer and Schmidt 1983). Despite the elegance of these complex organic compounds dissolved in organic solvents, it has been postulated that actinometric substances and solutions should be non-toxic and non-hazardous.

Immediately after various ultraviolet lamps became available in the beginning of the $20^{th}$ century, acidic iodide solutions have been used as chemical actinometers (Bering and Meyer 1912). The low quantum yield of 0.05 lead to the use of nitrous oxide ($N_2O$) as an electron scavenger (Dainton and Sills 1960, Rahn 1993). A more recent approach of opaque UVC actinometry is the iodate-stabilized photodecomposition of iodide (Rahn 1997, Rahn et al. 1999, 2003). The triodide formed from iodide photolysis at 253.7 nm is determined spectrophotometrically at 352 nm or higher wavelengths (375 nm, 400 nm). This system has the advantage of insensitivity to wavelengths over 300 nm.

The use of an actinometer solution has been proposed to replace UV-sensors by flow-through or static probes containing the actinometer solution, which are inserted into the irradiation reactor. The concentrated actinometer solution, e.g. the aforementioned iodide/iodate actinometer (U.S. Pat. No. 6,596,542) or an uridine solution (Schulz et al. 2001) is pumped through a UV-transparent tube receiving the UV light from the lamp, or contained in a cell with a transparent window facing the UV lamp to be exposed for a defined time, and the photoproducts are then measured in a spectrophotometer. These sensors, however, measure only the fraction of radiation incident on them, but not the average fluence (light dose) effective on the fluid to be irradiated while contained within the irradiation reactor.

In a rather limited number of cases, chemical actinometry has also been a method of choice to determine the number of totally absorbed photons or the effective light dose distribution in photochemical reactors and flash photolysis cells. In the pioneering phase of protein photochemistry in the 1950s, stirred batch cells were more frequently used for protein denaturation than for virus inactivation experiments (Rideal and Roberts 1951, Claesson 1956, Kleczkowski and Gold 1962), and uranyl oxalate actinometry was employed as standard method to determine the total incident quanta. Heidt and Boyles (1951) tested the effect of temperature and current on low-pressure mercury vapor-lamp UV-C-intensity for a 12 mL batch photoreactor using the uranyl oxalate actinometer. Engelhard and Eikenberg (1955) constructed a 50 mL batch recirculation cell for protein denaturation experiments and determined the absorbed UV photons by the chloroacetic acid actinometer. Taylor et al. (1957) and Oppenheimer et al. (1959) described the validation of the Centrifilmer irradiator by both off-line radiometry for lamp tests before use with an electronic tantalum photo-cell and absorbance-matching actinometry, based on quantum yield calculations, not on direct calibration, with uranyl oxalate. Apparently, no definitive results for the effective dose were obtained from this validation approach, as remarked upon the experimental treatment of liquid egg white in the Centrifilmer irradiator for the UV-C inactivation of *Salmonella* spp. (Ijichi et al. 1964), while at least the surface irradiant power could be determined by the use of radiochromic paper dosimetry (Launer and Hammerle 1964). Alfano et al. (1986a, 1986b), tried to confirm calculations for photochemical reactor modeling by chemical actinometry. Yokota and Suzuki (1995) tested an immersion-well photoreactor configured with multiple lamps by standard ferrioxalate actinometry. Recently, Vincze et al. (1999) noted that such an experimental verification procedure is still not common standard. von Sonntag (1999) described laser flash photolysis experiments, wherein a limited penetration depth of the incident light will result in a spatially uneven distribution of reaction products, nevertheless modeling calculations were applied for a simple rectangular photolysis cell, and to avoid absorption-matching actinometric procedures.

The disinfection of drinking water by UV-C light (Gelzhäuser 1985) has necessitated an actinometric validation of flow-through illuminators to ensure complete sterilization. In general, drinking water has a very low UV-C absorption as long as trace impurities such as Fe(III) or humic acids are absent. Therefore chemical actinometers based on decomposition of hydrogen peroxide (Kryschi et al. 1988) or tert-butanol sensitized potassium peroxodisulfate (Mark et al. 1990) have been developed. Another UVC sensitive actinometer is based on UV-induced hydroxylation of benzoate in alkaline solution to fluorescent dihydroxy benzoate (Moroson and Gregoriades 1964).

The use of a water-soluble triphenyl methane dye (4,4',4''-tris-di-β-hydroxyethylaminotriphenyl acetonitrile) as an added actinometer substance is described for the "cold-sterilization" of pathogens in fruit ciders, juices and plant saps by flow-through UV-C irradiation (Koutchma and Adhikari 2002, Adhikari et al. 2002). Equipment for this process is commercially available, e.g. the "Cidersure" or the "Sap Steady" thin-film irradiators manufactured by FPE Inc. of Macedon, N.Y., or the "Light Processed System" coiled tube irradiator manufactured by Salcor Inc., Falibrook, Calif. Ciders and juices obtained from squeezed fruits show high turbidity from suspended particles, and high UV-C absorption from dissolved phenolic compounds and from ascorbic acid, and also a viscosity similar to protein solutions. Clarified apple juice has an absorption coefficient of 9/cm at 253.7 nm. The actinometer substance is added to the highly absorbing juice and irradiated in a collimated-beam apparatus, as used for the absolute UV inactivation kinetics determination of microorganisms in non-absorbing suspension (Bolton and Linden 2003). The absorbance of the actinometer photoproduct at 600 nm increases, but in fact the added actinometer substance will only receive the light quanta fraction corresponding to its absorbance fraction of the total absorbance. The effective dose is then calculated from the destruction of the added actinometer dye. As it can be deduced from an "absorbed dose" of 190 mJ/cm$^2$ inactivating no more than 3 $\log_{10}$ colony-forming units (cfu) *E. coli* K12/mL in apple juice in a petri dish, the addition of an actinometer substance to the sample itself delivers obviously false results for the effective dose. In non-absorbing suspension, 5 $\log_{10}$ cfu/mL *E. coli* are inactivated at ~10 mJ/cm$^2$ (Wright and Sakamoto 1999). However, the dose effective in the solution must be the same as the dose effective on the microorganism. The proposed addition of an actinometer substance to an already absorbing medium is therefore not capable to accomplish an exact effective dose measurement.

A direct actinometric method to ensure the application of the correct amount of UV light in the virucidal flow-through UV-C treatment of protein solutions is based on their UV-C-induced UV-B absorbance increase (WO 03/007998). This absorbance increase is said to correlate with the inactivation of bacteriophage Phi-X 174, which is used as a biological dose indicator. A reverse-calibration of the absorbance increase to the corresponding bacteriophage titer reduction and even to the reduction equivalent dose (RED), can be done based on the obtained data, if a calibration plot using the dose-dependent titer reduction of bacteriophage Phi-X 174 has been established. However, the reduction equivalent dose (RED), which is the standard parameter determined in water UV-C disinfection, is not the same as the average dose effective in the fluid. The reduction-equivalent dose (RED) actually expresses a dose distribution which depends in the efficiency of mixing. Due to the decadic-logarithmic titer reduction of the bacteriophage, underirradiated volume fractions contribute more to the average residual bacteriophage titer than to the actinometric magnitude of the average effective dose, which usually shows an ideally linear concentration-dependent change by the converted light photons.

The biological dosimetry using a photoinactivatable microorganism was the first method to determine the applied dose in the irradiation of plasma (Oliphant and Hollaender 1946), although details on the dosimetry using Aerobacter aerogenes (outdated name for *Klebsiella pneumoniae*) were not given. During use of UVC for the inactivation of serum hepatitis virus, this bacterial strain was used to validate thin-film irradiators (McCall et al. 1957). In addition, single-stranded DNA bacteriophages of the microviridae family such as S13 (Latarjet and Wahl 1945) and Phi-X (phi chi) 174 (Setlow and Boyce 1960) give a linear decrease of titer with an increasing UV irradiation dose. Biodosimetry based on the inactivation of bacteriophages (e.g. Phi-X 174 (Battigelli et al. 1993) or the single-stranded RNA bacteriophage MS2 (Havelaar et al. 1991)), or the inactivation of *Bacillus subtilis* spores, has been developed for testing flow-through ultraviolet water disinfectors (Sommer et al. 2001). An absorption coefficient of water can be adjusted with dissolved sodium thiosulphate so that the coefficient reduces UV transmissions (Cabaj et al. 1996). Nevertheless, an electronic radiometer at the end of this light path and efficient flow-through mixing to narrow dose distributions (Cabaj and Sommer 2000) is still required for this method, and the incubation time for spore cultivation does not allow for rapid validation.

The validation of flow-through irradiators for ultraviolet irradiation in a combined beta-propiolactone and ultraviolet "cold sterilization" of plasma proteins also has used bacteriophages (Dichtelmüller and Stephan 1988). However, these processes are limited by fast-flowing fractions with lower and potentially insufficient doses (Qualls and Johnson 1983).

Only liquid layers very thin in relation to the light absorption don't require a fluence rate correction for self-absorption. Otherwise, the decline in fluence with the distance has to be calculated (Morowitz 1950). The effects of light absorption of virus suspensions on UV-C-inactivation kinetics was investigated in pioneer experiments in a side-illuminated 1.5 cm-diameter quartz cell (Taylor et al. 1941). The cell was stirred slowly, and a deviation of the inactivation kinetics, linear at a concentration of 10 µg virus/mL, was observed already at 20 µg/mL and at 200 µg/mL. Using stirred top-illuminated petri dishes, it was demonstrated that shielding of viruses in stagnant deeper layers, into which the light could not penetrate at its initial intensity, was avoided when a virus suspension was stirred, so that the virus inactivation kinetics remained linear (Budowsky et al. 1981).

Parameters of the latest designs of whole blood irradiators have been validated by Ternovoy et al. (1988). Actinometry using water-soluble diazonium salts was chosen to compare efficiencies of thin-film cells or capillary devices. The apparatus described did not exceed an internal diameter of 3 mm and are constructed to expose a maximum internal surface to the UV light. Both high protein concentrations and cellular components absorb incident light at the surface, and laminar flow profiles in the cells or cylinders makes dose distribution more uneven, exposing slow-flowing outer layers to higher UV irradiances compared to faster-flowing inner volumes. Therefore such devices are unsuitable in the context of pathogen inactivation of biological substances.

Most blood plasma irradiation devices are based on a thin-film principle, which limits sample throughput. However, high-throughput irradiators have been developed with liquid layer thicknesses exceeding those UV-C penetration depths seen in the past.

For example, a thin-film irradiator manufactured by Dill Instruments Co. is a widely used instrument for irradiation of biological fluids. In particular, U.S. Pat. No. 5,567,616 describes an inclined, externally illuminated and UV-translucent rotating cylinder enabling biological fluid to flow by gravity downward along an inner wall. Two light sensors, mounted at the upper end on an outer surface and in an inner cavity, measure light intensity transmitted by a fluid film and the film thickness. The Dill irradiator has been used for the beta-propiolactone/UV process and for irradiation of fibrinogen preparations stabilized with cystine (McCall et al. 1957) or rutin (Marx et al. 1997).

U.S. Pat. No. 5,133,932 discloses an UV-C irradiation method for pathogen inactivation in a baffled vessel rotating horizontally around its axis, in which the biological fluid is contained in a lower reservoir and dispersed to form a thin film on the inner wall upon rotation, which is then re-mixed with the reservoir. This principle of a thin-film mixed-batch irradiator has already been applied by Oliphant and Hollaender (1946). In the disclosed invention, the UV-C lamps are inserted into the vessel's neck and mounted parallel to the rotation axis. Only a small volume fraction of the vessel can be filled with the fluid, thus reducing the capacity and the scalability of the method.

U.S. Pat. No. 6,190,608 describes a flow-through method to treat blood products with UV-C radiation to inactivate erythrovirus B19, because, as described above, parvoviruses are susceptible to low doses of UV radiation. In a straight flow-through quartz or UV-C-transparent plastics tube, a turbulent flow can be generated by obstacles or nitrogen bubbles. The UV intensity is adjusted by means of a filter between a lamp and the quartz tube, and UV irradiance is measured by an electronic radiometer. The UV dose is adjusted by setting the flow rate for an appropriate exposure time.

U.S. Pat. No. 6,540,967 discloses an inclined, UV-translucent, and internally illuminated rotating cylinder with the liquid flowing downward by gravity on the outer surface. The film-thickness of the liquid layer is controlled by an interferometer. This apparatus is proposed for inactivation of viruses and mycoplasms in biological fluids.

U.S. Pat. No. 6,586,172 discloses a UV-C transparent flow-through cell wherein a static axial mixer provides sufficient mixing to ensure an equal irradiation of the sample. A method of validation also is disclosed, which uses daylight-insensitive aqueous iodide solutions for monitoring of apparatus irradiance from UV lamps by spectrophotometry of formed tri-iodide at 352 nm (Hackradt 1920, 1922, Rahn 1993). In the examples given in the corresponding WO 00/20045, a 1% NaI solution is used for all products regardless of their UV-C absorption coefficient, such as 4.5% albumin solution, plasma, or concentrated immunoglobulin solution. Neither absorbance nor viscosity of the protein solutions are matched and failure of actinometric lamp monitoring in determination of applied UV dose or equivalent dose effective in the protein solution is therefore evident by use of empirical constants in the dose/inactivation equation. In this connection, to ensure an effective pathogen inactivation with a static mixing apparatus, model calculation parameters such as flow rate, device length, and residence time have to be optimized experimentally.

In general, a known disadvantage of using iodide solutions is low quantum yield of photochemical reaction and nonlinear dose-response (Rahn 1997). For on-line processes, radiometers would enable a time-resolved UV intensity measurement as an indicator of lamp ageing and short-time radiance changes.

WO 01/74407 discloses a portable flow-through device for inactivation of pathogens especially in single donations of blood or blood plasma by UV-C irradiation. This device can be validated using a 1% NaI in 20 mM Tris buffer actinometer, however, this the high absorbance of this actinometer is used to determine an "absolute dose" expressed as energy applied per volume ($J/m^3$). This, however, does not conform to the photochemical concept of fluence as the energy incident on and only partially absorbed by an area (Bolton 1999). Historically, all such experiments of virus inactivation have been performed in buffer suspensions spread in thin films over an area to express the fluence in $erg/mm^2$, $mJ/cm^2$ or $J/m^2$, so that comparison of various methodologies would require fluence data.

US patent application 2003/0049809 A1 discloses a method for the flow-through UV-C inactivation of microorganisms in a fluid, where a secondary flow is superimposed in the helically coiled tube wound around the UV-C lamp. The example of parvovirus inactivation in $\alpha_1$-proteinase inhibitor solution at different protein concentrations has been given, as well as the evaluation of the reactor by the use of the iodide/iodate actinometer solution (Rahn 1993, 1997). Both the titer reduction at a pre-defined UV fluence, which decreases at higher protein concentrations, and the term "light yield" given for the actinometric test result demonstrate that the accurate dose effective in the protein solutions can't been determined by the use of a concentrated actinometer solution.

U.S. Pat. No. 6,329,136 discloses a method for pathogen inactivation in biological fluids using a 20 ns-laser pulses at 248 nm. The experimental setup consists of a KrF excimer laser with its beam targeted at a cylindrical 1 cm quartz cell containing the stirred sample solution. The energy applied is measured by a electronic sensor and expressed as the fluence ($mJ/cm^2$). The fluences necessary for inactivation of viruses in buffer and protein-containing solutions are remarkably different. As it is stated in the description: "The pulsed UV dose at (248 nm) required to eliminate [Blue Tongue virus] BTV from fetal bovine serum, as compared to [phosphate-buffered saline] PBS, is 15 times greater. This difference is perhaps due to the optical properties of the host media (i.e. optical transparency). In PBS, the buffered saline media is an optically clear aqueous solution, whereas fetal bovine serum is a less transparent, complex colored solution which contains UV absorbent chemicals, such as proteins, which do absorb some of the 248 nm UV light energy", it is apparent that high UV-C absorption of matrix proteins reduces sample volumes effectively illuminated by the incident UV laser light.

U.S. Pat. No. 6,576,201 discloses a cylindrical UV-C transparent flow-through cell with a static outer transparent wall and a turning inner cylinder. In a liquid layer in between, the liquid pumped through the cell is mixed by counter-current Taylor vortices. A continuous-wave or a pulsed laser-UV source is disclosed for illumination.

Similar Taylor-vortex generating devices has also been investigated as photochemical reactors for heterogeneous and homogeneous photochemical processes (Sczechowski et al. 1995, Forney and Pierson 2003). For the actinometric examination of the reactor, either the ferroixalate (Kirk and Mamasivayam 1983) or the iodide/iodate actinometer (Rahn 1997) were used. The iodide-iodate actinometer was also diluted up to 100-fold to reduce the iodide concentration for the examination of the relationship of the outlet triiodide concentration to the inlet iodide concentration (Forney and Pierson 2003). The relationship of the outlet triiodide concentration to the flow-rate dependent 254 nm photon dose was determined using a fixed absorbance of the actinometer solution, and a theoretical calculation based on the lamp geometry, the flow-rate, the quantum yield and the photon energy. However, an absorbance-matching calibration to determine the dose effective in the iodide solution was neither proposed nor done ((Forney and Pierson 2003).

WO 97/33629 discloses a process for sterilization and purification of biological fluids by exposure to UV radiation between 200 nm and 250 nm.

In 1960, one of the leading experts in thin-film UV-C-irradiated vaccine technology stated: "In order to calculate the absolute quantity of energy involved in the virus inactivation itself, there must be some manner of quantitating the relative amounts of ultraviolet energy absorbed by the virus and the culture medium. This has not been possible as yet; furthermore the absolute exposure is dependent upon a number of variable factors: viscosity, temperature, surface tension, and frictional resistance of flow" (Taylor 1960). Prior to the present invention, the scientific or patent literature still fails to disclose a determination of the photochemically effective dose on pathogens in a fluid sample. Accordingly, a method for the inactivation of pathogens in a biological fluid is desirable. A method for determining a photochemically effective dose of electromagnetic radiation, such as light, sufficient to inactivate pathogens in a biological sample while leaving biologically active substances of interest unaffected is also particularly desirable.

SUMMARY OF THE INVENTION

The present invention provides a method for the inactivation of pathogens in a biological fluid. The present invention also provides a method for determining a photochemically effective dose of monochromatic or polychromatic light to inactivate pathogens in a fluid.

Accordingly, the instant invention provides the methods for inactivation of microorganism in a biological fluid, comprising irradiating the biological fluid with an effective dose of monochromatic or polychromatic light from one or more light sources, wherein the effective dose is determined by measuring the effect of monochromatic or polychromatic light on a dosimetric, solution matching the absorbance or the absorbance and the viscosity of the biological fluid at the photoinactivating wavelengths used, in order to determine an effective dose.

In particular, in one embodiment, the invention provides methods for the photoinactivation of microorganisms in a biological fluid, comprising irradiating the biological fluid with an effective dose of monochromatic or polychromatic light from one or more light sources, wherein the effective dose is determined by, in any order, measuring the effect of the monochromatic or polychromatic light on an absorbance-matching or absorbance- and viscosity-matching chemical dosimetric solution; measuring the biodosimetric inactivation based on the chemical dosimetry of a photoinactivatable microorganism added to the biological fluid; and monitoring and recording the intensity of the light source or sources by radiometry to check and correct for changes in light source intensity.

In another embodiment, the invention provides methods for the determination of the degree of mixing for the photo-inactivation of microorganisms in a biological fluid, comprising: irradiating a chemical dosimetric solution matching the absorbance or the absorbance and the viscosity of the biological fluid to determine the dose of monochromatic or polychromatic light effective in the biological fluid at defined mixing conditions; measuring the biodosimetric inactivation rate based on the chemical dosimetry data of a photoinactivatable microorganism added to the biological fluid at the same defined mixing conditions; monitoring and recording the intensity of the light source or sources by radiometry in the dosimetry and biodosimetry experiments to check and correct for changes, if needed, in light source intensity; to obtain mixing conditions from the radiometry-corrected dosimetric and biodosimetric results where a maximum inactivation rate of the microorganism is achieved at the feasible minimum inactivation of or damage to the substances of interest in the biological fluid.

In another embodiment, the invention provides methods for determining an effective dose of monochromatic or polychromatic light from one or more light sources to inactivate microorganisms present in a biological fluid, comprising measuring the effect of monochromatic or polychromatic light on a dosimetric solution matching the absorbance or the absorbance and the viscosity of the biological fluid at the photoinactivating wavelengths used.

The instant invention also provides methods for determining dose by titrating viable microorganisms before, during and after irradiating said biological fluid. The sample may be spiked with viable organisms before or during irradiation.

The intensity of the one or more light sources may be monitored during irradiation in order to determine an irradiating dose. The light may be in the UV range.

In particular, the invention provides methods for determining the effective doses of monochromatic or polychromatic light from one or more light sources to inactivate pathogens present in a biological fluid, and the time necessary to apply such a dose, and the target lamp dose equivalent to the light dose effective in the fluid, wherein the effective dose is determined by: irradiating a chemical dosimetric solution matching the absorbance or the absorbance and the viscosity of the biological fluid to determine the dose of monochromatic or polychromatic light effective in the biological fluid; and monitoring and recording the intensity of the light source or sources by radiometry at the dosimetry experiments to check and correct for changes, if needed, in light source intensity, and to sum up the lamp intensity signals over the irradiation time to obtain the target lamp dose. The light can be in the UV range.

The dosimetric solution can comprise agents selected from the group consisting of alkali metal, alkaline earth metal and ammonium iodide, aqueous uridine phosphate, alkali metal, alkaline earth metal and ammonium salts of benzoic acid, and alkali metal, alkaline earth metal and ammonium peroxodisulfate.

In a preferred embodiment of the present invention, the dosimetric solution can comprise a diluted absorbance-matching potassium iodide-potassium iodate actinometer or a diluted and absorbance- and viscosity-matching potassium iodide-potassium iodate-polyvinylpyrrolidone actinometer. The dosimetric solution may comprise a diluted absorbance-matching sodium benzoate actinometer. The dosimetric solution may also comprise a diluted absorbance-matching potassium peroxodisulfate/tert-butanol actinometer.

Biodosimetry may be performed on linear or circular single-stranded nucleic acid viruses such as single-stranded, non-lipid-enveloped viruses comprising the Parvoviridae family of DNA viruses (e.g. Murine Minute Virus (MMV), Canine Parvovirus (CPV), Bovine Parvovirus (BPV), Porcine Parvovirus (PPV), Feline Parvovirus (FPV)), Circoviridae and Circinoviridae family of DNA viruses (e.g. Transfusion Transmitted Virus, TTV), Picornaviridae family of RNA viruses (e.g. Hepatitis A virus (HAV), Encephalomyocarditis Virus (EMV)), Enteroviridae family of RNA viruses (e.g. Poliovirus), Microviridae family of DNA bacteriophages (e.g. S13, alpha 3 and Phi-X 174), and Leviviridae family of RNA bacteriophages (e.g. MS2).

The biological fluid can be contained for example in stirred-batch photoinactivation reactors. The biological fluid may comprise at least one additive to reduce damage and loss of biological activity of said fluid.

The method can be performed in conjunction with at least one other sterilization or microorganism inactivation method. The method may also be performed with a solvent detergent treatment.

In another embodiment, the invention provides a batch irradiation reactor comprising an upright irradiation vessel with a wall transparent to a photoinactivating light wavelength, a stirrer within the vessel capable of mixing a volume of material placed within the vessel by moving fractions of the volume to and away from an irradiation zone, one or more light sources thermostated to emit a constant radiance of the photoinactivating wavelengths into the irradiation vessel, and an electronic monitoring device with a sensor sensitive to the photoinactivating wavelengths.

Preferably, the light sources of the instant batch reactor may be equipped with reflectors to reflect light onto a transparent wall of the irradiation vessel. The light sources may be switchable individually. Preferably, radiometer signals emitted by the sensor are summed up to a target value by means of a mechanical, electronic or computer-software-controlled counter. One or more light sources may be turned off automatically when energy from the photoinactivating wavelengths has reached a target value. The light sources may be mounted externally. The light sources may be thermostated by a cooling liquid. The reactor may be equipped with a stacked impeller stirrer, preferably with near-wall wiper blades.

In another embodiment, the instant invention provides a device for calibration comprising: a light source, a light exit aperture allowing the light to radiate into an collimator aperture, a shutter, and a slot mounted in a thermostated housing with a light entrance aperture allowing light to radiate onto a sample, which may be contained in a cuvette. Preferably, the device further comprises at least one radiometer sensor attached to a mount, wherein light radiates from the light source simultaneously through both the shutter onto the sample and through the aperture onto the radiometer sensor.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The accompanying drawings, which are incorporated in and constitute a part of the specification, illustrate one embodiment of the invention, and, together with the general description given above and the detailed description of this embodiment given below, serve to explain the principles of the invention. Thus, for a more complete understanding of the present invention, the objects and advantages thereof, reference is now made to the following descriptions taken in connection with the accompanying drawings in which:

FIG. 10 depicts an exemplary calibration device of the instant invention.

DETAILED DESCRIPTION OF THE PREFERRED EMBODIMENTS

Figure 1:
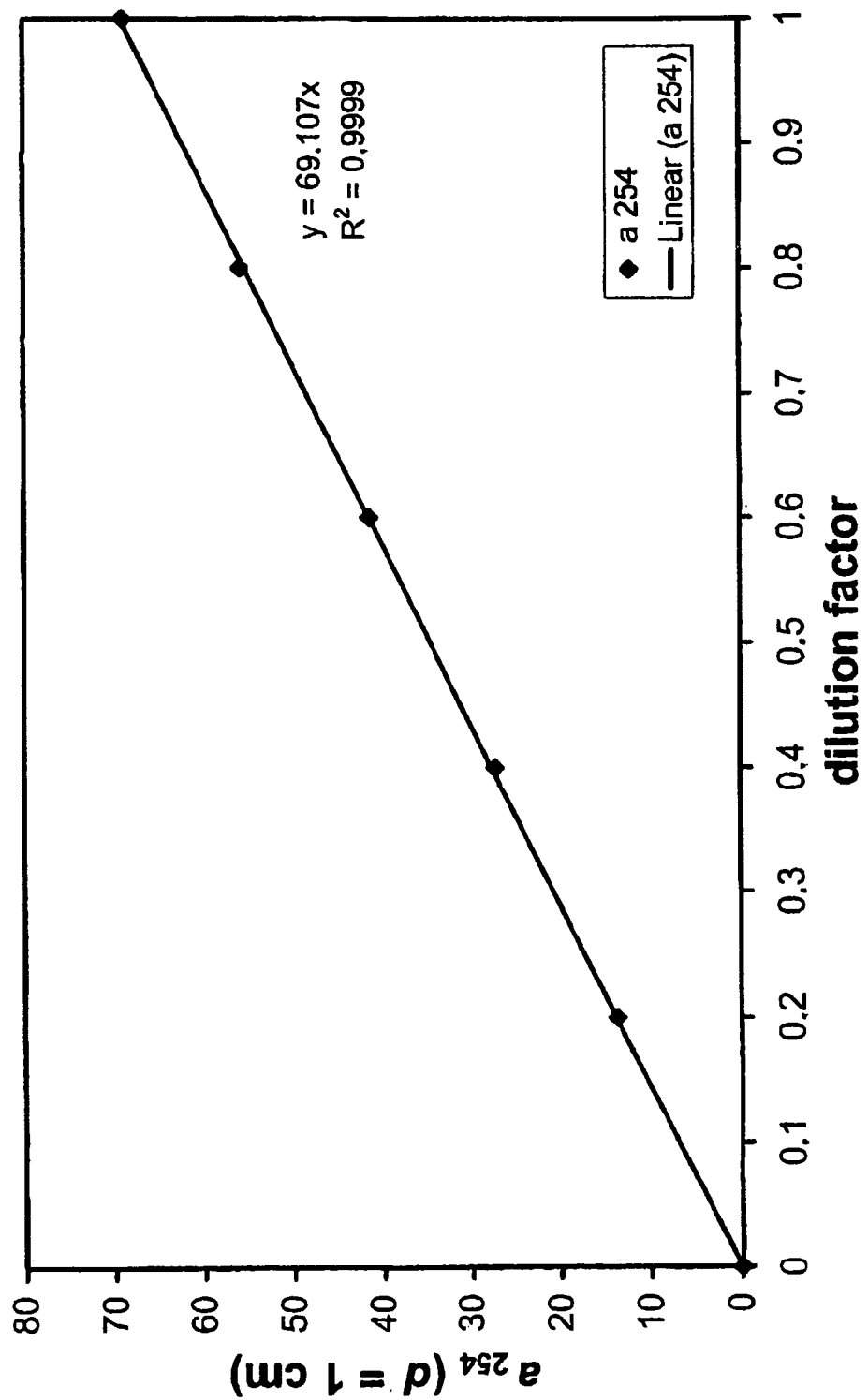
FIG. 1. depicts the linear relationship between an absorption coefficient and concentration.

A microorganism refers to any unicellular eukaryotic organism, such as yeasts, protozoans and to any prokaryotic organism, such as bacteria, or to any virus infecting humans, animals, fungi, plants or prokaryotic unicellular organisms as its host.

Light, monochromatic light, or polychromatic light refers to energy in the electromagnetic spectrum, preferably those wavelengths and frequencies within the UV and visible range.

A biological fluid refers to any fluid derived from blood or blood products. Furthermore, it refers to other biologically derived fluids, such as those comprising milk, whey and milk protein fractions, and the whole fluid and fractions of spinal fluid, lymph, saliva, semen, urine, egg, prokaryotic cell culture supernatant, eukaryotic cell culture supernatant, prokaryotic cell lysate, eukaryotic cell lysate, native plant sap or transgenic plant sap, and native plant fruit juice or transgenic plant fruit juice. Preferably, biological fluids include blood, plasma, plasma fractions, serum and fluids derived from blood, plasma and serum. Biological fluids and the derivatives thereof may be of therapeutic, cosmetic, or nutritional value and use.

Biological fluids may contain natural or artificially added substances, which do not affect the nucleic acid photodamage to the pathogens, but which may exert a beneficial protecting effect to preserve the components of interest upon light irradiation, and most notably upon UV-light irradiation, by acting as reactive oxygen radical quenchers, e.g. flavonoids such as rutin (Erdmann 1956, WO94/28210), vitamins such as ascorbic acid (Erdmann 1956), and creatinine (JP 11286453-A). However, if these additives supplement an additional absorbance at the wavelength used, too little pathogenicidal light energy may actually reach the pathogens, if the additional absorbance is not compensated in the applied light dose. An excess of applied energy readily damages the proteins, and it is therefore necessary to not exceed the UV or visible light dose required for sufficient pathogen inactivation, and to calculate or determine this dose as accurately as possible.

In one embodiment, the effective does is measured using chemical dosimetry by the effect of monochromatic or polychromatic light on an dosimetric solution. A dosimetric solution is a solution prepared from reagents which undergo a substantial photochemical reaction at the wavelengths to be measured, thereby generating a photoproduct that can be measured. The photoproduct can be measured with sufficient sensitivity in layers thin in relation to the Napierian absorption coefficient of the solution, so that only a small fraction of the incident radiation is absorbed within this layer, thereby enabling a fluence determination since light energy radiating onto an area of a layer passes the layer practically unabsorbed.

A number of chemical actinometers are known to those of ordinary skill and are sufficient to practice the invention. For example, a dosimetric solution suitable for the UV-C irradiation may be selected from the group consisting of alkali metals, alkaline earth metal and ammonium salts of iodide, and aqueous uridine phosphate.

It is an aspect of the present invention, that the method for inactivation of pathogens allows to use a dosimeter solution with a predetermined absorbance at the irradiation wavelength, or such a predetermined absorbance and a predetermined viscosity, in order to match the absorbance or both the absorbance and the viscosity of the biological fluid to be light-irradiated for pathogen inactivation.

A number of UV-C-sensitive chemical dosimeters especially suitable for concentrated, i.e. highly absorbing, biological fluids may be used with the instant invention. For example, diluted potassium iodide-potassium iodate actinometers (for example, but not limited to, containing $\geq 6.96$ mM KI and 1.16 mM $KIO_3$) possess a high absorbance corresponding to the absorbance of such a biological fluid (for example, but not limited to, $a_{253.7} \geq 2/cm$), a high quantum yield, and a high specific extinction coefficient of triiodide. This dosimeter solution can be prepared with the corresponding concentrations of potassium iodide and potassium iodate to match absorption coefficients of biological fluids preferably, but not limited to, with an absorption coefficient $a_{253.7} \geq 2/cm$, and it is usable in thin layer cuvettes, preferably, but not limited to, with an optical path length of 0.1 to 1 mm. By the addition of polyvinylpyrrolidone (PVP), which is known for its stabilizing effect on tri-iodide, the sensitivity of the iodide/iodate solution is increased, and the viscosity of the protein solution is matched with great accuracy.

Another preferable UV-C-sensitive chemical dosimeter especially suitable for dilute, i.e. low-absorbing, biological fluids is a sodium benzoate actinometer, which allows fluorimetric determination of the photoproduct in a thin layer-fluorescence cell, and which may be diluted for example, but not limited to, to match absorption coefficients, $a_{253.7}$ from 0.1/cm to 2/cm for thin-layer fluorescence cuvettes preferably, but not limited to, with a path length of $\geq 1 \times 10$ mm.

Still another preferable UV-C-sensitive chemical dosimeter especially suitable for very dilute, i.e. almost non-absorbing biological fluids is a potassium peroxodisulfate/tert-butanol actinometer, which also may be diluted to match absorption coefficients preferably, but not limited of to, $a_{253.7} \leq 0.5/cm$. The dosimeter solutions may preferably, but not limited to, be used in cuvettes with 0.5 to 1 cm path length. The photoproduct, hydrogen ions, may be measured using a pH meter by immersion of a suitable, preferably miniaturized, pH electrode.

The decadic absorption coefficient of a biological sample solution may be measured in a spectrophotometer in a cuvette sufficiently thin to keep the absorbance within the spectrophotometer's measurement range. The absorption coefficient is calculated by dividing the result by the path length (typically in centimeters), and the Napierian absorption coefficient by multiplying the decadic absorption coefficient with the natural logarithm of 10.

The viscosity may be determined by measurement of the flow-time in a capillary viscosimeter and multiplying the result with the capillary viscosimeter constant.

The light path length of the thin-layer cuvette used with the absorption-matching diluted actinometric solutions may be kept small, so that only a small fraction of incident light is absorbed within the cuvette.

By calibrating using partially-absorbing diluted actinometric solutions in such thin layers, fluence can be applied with the greatest accuracy possible. The absorption may be, for example, 27.3% for a solution with the decadic absorption coefficient at 253.7 nm $a_{253.7}=15/cm$ in a 0.02 cm cuvette, or 19.9% for a solution with $a_{253.7}=2/cm$ in a 0.1 cm cuvette, which means that the dose effective through the light path length is 72.7% of the incident irradiant energy for the first and 80.1% for the latter (Morowitz 1950). So the Morowitz correction factor is 72.7% for the first given example and 80.1% for the other. The self-absorption error can thus be easily calculated and corrected. For an accurate calibration, it is in general advisable not to use Morowitz correction factors below 50%, which means that the cuvette path length should not exceed the distance, where the light intensity has been reduced to 25% of its initial value.

For establishing a dosimetric calibration plot, a light source with a known irradiance may be measured, for example, by electronic radiometry, spectroradiometry, or chemical actinometry with a concentrated and fully-absorbing actinometer solution. After determination of the irradiance incident from the light source, a cuvette containing the diluted absorbance-matching or absorbance- and viscosity-matching dosimetric solution is irradiated at a defined geometry and irradiance for a defined time to apply a defined surface dose, and the obtained actinometric signal is measured and plotted against the light dose.

This calibration can be accomplished by using, for example, a lamp, a shutter within the light path to expose the cuvette for a defined exposure time, and a cuvette mounted parallel to the lamp at the end of the light path. Such shutters are used, for example, as film-plane shutters in photographic cameras, and the shutter mechanism is accurately controlled by mechanical clockwork, or preferably by an electronic oscillator. The oscillator-driven shutter and the fixed cuvette position ensure a reproducible and accurate exposure of the cuvette. To produce this, a commercially available 35 mm or medium format film single-lens reflex or rangefinder camera body can be modified by attachment of a lamp fixture to the camera lensmount, and attachment of a cuvette to an aperture milled into the camera back. Preferably, the aperture in the camera back itself has the dimensions such that the entire surface of the cuvette is illuminated, while the edges of the aperture act as a partial collimator. To improve stability of lamp intensity and the actinometric quantum yield, the lamp and the cuvette insert can be thermostated by such devices such as a fan, a circulating liquid, or a Peltier element.

Such a device for calibration also can be used to check and re-calibrate radiometer sensors by attaching a mount for a radiometer sensor to the lamp fixture, so that light emitted from the lamp can be measured simultaneously by the actinometer cuvette and the radiometer sensor.

For measurement of an effective light dose, a volume of the dosimetric solution equal to the product volume is irradiated in the irradiation device, and a small sample volume is drawn at a defined time and filled into the thin-layer cuvette, and the light-generated reaction product is measured. The signal obtained from the irradiated dosimetry solution used is recorded, and compared with the corresponding calibration plot. The dose is then calculated as dose-increase divided by the irradiation time unit. For a reactor with fixed geometry, the irradiation time is a linear function of the absorbance.

The calibration of an UV-C irradiation device by absorption and viscosity-matching chemical dosimetry can be done experimentally on a very simple UV-C thin-film irradiator with a mixed batch reservoir, such as a stirred upright quartz bottle or quartz test tube filled with a UV-C-absorbing protein solution and illuminated with a low-pressure Hg vapor lamp from the side.

The chemical method of dosimetry with actinometric solutions can measure an average light dose (fluence) applied to the sample volume filled into a thin-layer cuvette. In this regard, the photochemical reactants are usually present in excess, any local surplus of the photochemical reaction product is readily mixed and diluted, and the concentration of the reaction product increases in an ideally linear ratio to number of photons applied.

In another embodiment, the biologically effective light dose (fluence) is determined by biodosimetry, which refers to a determination by the photoinactivation of microorganisms. Biodosimetry can be done with flow-through-irradiation devices and has been conventionally used as a suitable method for measurement of residence time distribution (Qualls and Johnson 1983) and light dose distribution (Cabaj and Sommer 2000).

Generally, the same number of photons will inactivate the same fraction of viable microorganisms per volume or titer, and any decrease in the logarithm of the titer is linear. Furthermore, a local excess of light intensity cannot reduce the number of viable microorganisms to less than zero, while a locally insufficient light dose will leave a residual number of viable microorganisms present in the sample. In an optically opaque liquid irradiated in a batch or flow-through photoreactor, the microorganisms will pass the shallow illuminated outermost volume layers only for a very short time, and will remain shielded for the greater fraction of the treatment time.

In a preferred embodiment, biodosimetry may be used in combination with chemical dosimetry to determine mixing efficiency. In this regard, a more efficient method with a higher degree of mixing will narrow the residence time distribution and increase the inactivation rate. Such a higher degree of mixing can be achieved using a stirrer with more than one impeller mounted along the stirrer axis, and more preferably, for liquids with higher viscosity, with additional outer wiper blades extending along the entire stirrer length parallel to the stirrer axis, which leaves a gap between the their outer edge and the inner vessel wall sufficiently narrow to generate additional turbulence near the irradiation zone.

In another embodiment, the invention provides for the monitoring of one or more light sources. Radiometric monitoring of a light source is a conventional practice for flow-through devices. Lamp power can be continuously monitored and the signal displayed or recorded.

In another preferred embodiment, the entire volume to be treated is confined within the irradiation reactor and radiometric signals may be summed up during the process to a final radiometric target lamp dose, which may depend on the absorption coefficient and increase with irradiation time.

Generally, a common low-pressure mercury vapor lamp loses at least 15% to more than 50% of initial UV-C (253.7 nm) intensity during a lifetime. Preferably, the dose-rate at a known lamp power is determined and the lamp power measured. In this way, the dose-rate can be normalized to the lamp power. The lamp power can be multiplied by the irradiation time and will give a target lamp dose.

By the use of chemical dosimetry, biodosimetry, and radiometry in combination, the following parameters are determined to optimize the batch irradiation process: At constant lamp radiance, chemical dosimetry delivers the basic information about the average dose (fluence) effective in the fluid, the dose-rate (fluence increase/time interval), and irradiation time depending on the fluid absorbance. Biodosimetry determines the mixing efficiency by microorganism inactivation rate (reduction of titer per chemically determined dose unit) and allows determination that the effective dose was able to inactivate the microorganism to the desired extent. Radiometry corrects for variability in lamp radiance and delivers the total radiometric target lamp dose as a summed-up irradiance over the irradiation time, which is simultaneously determined by chemical dosimetry. An optimized process can thus be designed and evaluated to ensure minimum photodenaturation of the substances of interest and maximum pathogen inactivation.

The following variables are used in the linear relationships described below:
Absorption coefficient: "a" (1/cm)=measure of light intensity reduction along a light path length at a defined wavelength;
Irradiation time: "t" (s);
Lamp power: "P" (mW/cm$^2$)=radiant power emitted by the lamp;
Effective light dose: "$H_0$" (mJ/cm$^2$)=fluence effective on a cross-section of a volume in the irradiated fluid over the irradiation time;
Lamp dose: "Q" (mJ/cm$^2$)=radiant energy emitted by the lamp over the irradiation time;
Radiometric target lamp dose: "Q'" (mJ/cm$^2$)=irradiant energy emitted from the lamp and incident on a radiometer sensor over the irradiation time.

These photochemical variables are related by the following linear relationships:

$$t = k_1 \times a$$

$$Q = P \times t$$

$$Q' = Q_1 + Q_2 + Q_3 + \ldots + Q_n = \Sigma_i Q_i = \Sigma_i P_i \times t$$

$$Q' = k_2 \times a$$

$k_1$ and $k_2$ are empirical reactor-geometry and mixing-efficiency-specific constants which can be derived from experimentation, as illustrated in example 2 for $k_1$, and in example 6 for $k_2$, respectively. For routine operation of a batch photoreactor, it is only necessary to know this relationship between the absorption coefficient and irradiation time or the radiometric lamp dose to determine an effective target light dose.

In a preferred embodiment, chemical dosimetric solutions, such as iodide/iodate in borate buffer, are adjusted to i) the same absorbance at 254 nm, particularly at 253.7 nm, by dilution and ii) to the same viscosity, by, for example, addition of polyvinylpyrrolidone, as the desired target protein solution. In this way, chemical dosimetric solutions will determine a percentage of irradiating light effectively used to generate triiodide, which can be measured complexed with polyvinylpyrrolidone at 367 nm. The percentage of light can be calculated in theory for very simple irradiation devices, e.g. an 1 cm cuvette, by integration of the intensity (I) as determined by Lambert-Beer's law of absorption (Morowitz 1950):

$$I(d) = I_0 \times \exp(-\alpha \times d) = I_0 \times \exp(-a \times \ln 10 \times d)$$

wherein
I is intensity, depending on length d (in cm); and
a is the decadic absorption coefficient (units: 1/cm), wherein $a = -\log_{10} T = -\log_{10}$ transmission. Accordingly, an absorption of 1.0 means that a $10^1$ part or 10% of the light is transmitted, while 90% is absorbed. When $\alpha$ is the Napierian absorption coefficient, then $\alpha = a \times \ln 10 = a \times 2.303$.

By integration of Lambert-Beer's law, a liquid (in a 1 cm cuvette) with a Napierian coefficient of at least $\alpha_{253.7} = 10/cm$, the $\sim 1/\alpha$ part of the incident light intensity is effective to inactivate the target microorganisms.

For a virucidally effective UV-C dose of 20 mJ/cm$^2$ and an incident UV-C intensity of 1 mW/cm$^2$, then the relationship 1 (mJ/cm$^2$)/s exists. Accordingly, where $\alpha = 10/cm$, then 1 s×20×10=200 s, where $\alpha = 25/cm$, then 1 s×20×25=500 s, where $\alpha = 40/cm$, then 1 s×20×40=800 s.

To establish a dosimetric calibration plot, the chemical dosimetry solution is spread into a thin film of defined depth, and absorbs only a small fraction of incident light. The film is exposed to a light dose and undergoes a substantial and quantifiable change by conversion of a chemical species to yield a light absorption or a fluorescence emission at a defined wavelength, or a pH increase. The actinometric signal is measured and plotted against the light dose.

The corresponding solution may then be irradiated in a mixed batch volume, and a volume is drawn and the light-generated reaction product is measured. The signal obtained from the irradiated dosimetry solution is recorded and compared with the corresponding calibration plot. This will yield an effective dose corresponding to a signal increase in the dosimetric calibration plot. The dose rate is then calculated as dose-increase divided by the irradiation time unit. The effective dose is the dose which inactivates substantially all of the target microorganisms in said biological fluid.

The dosimetric solution simulates a target protein solution since the dosimetric solution has the same absorbance at defined wavelengths as the protein solution. Measuring conversion of chemical species formed by light, such as triiodide, can be correlated with an effective UV-dose. Chemical dosimetry ensures that protein solutions with different absorbances will receive the same effective UV dose.

The protein solutions or the other biological fluids may be spiked with non-pathogenic or pathogenic fungi, single-cell protozoa, bacteria, preferably with viruses or bacteriophages to ensure that such or similar pathogens are killed or reduced in activity. To ensure that the components of interest such as proteins and other important biological molecules are preserved, the biological activity of the proteins or e.g. of vitamins may be measured.

The dosimetry reagents are small dissolved molecules present in a considerable excess, which will easily diffuse to the irradiated zone. Accordingly, the dosimetry reagents will be converted by the incident light photons to the photochemical reaction product. With lamps operating at constant intensity, the same number of light photons will be irradiating the reactor volume and apply the same effective dose (mJ/cm$^2$) in a given time interval to yield a chemical dose rate ((mJ/cm$^2$)/min). Intensity of the lamps may be taken into account by controlling the total irradiating lamp dose. For a protein solution with bacteriophages or viruses, the dose rate will be the same for a given absorbance and viscosity.

Microorganisms, such as bacteriophages, viruses, and bacteria ideally exhibit exponential decay in viability. This means that a given dose will inactivate the same fraction of viable microorganisms. For example, if 1 mJ/cm$^2$ reduces the initial titer to $\frac{1}{10}$th, then 2 mJ/cm$^2$ to $\frac{1}{100}$th, 3 mJ/cm$^2$ to $\frac{1}{1000}$th, and so on. If all microorganisms were exposed equally by transporting all microorganisms only once to the irradiation zone, then all microorganisms would receive an inactivating hit. However, even the smallest microorganisms such as single-stranded DNA bacteriophages are large particles (~25 nm) compared to proteins, and are moved by convection and flow of the protein solution. In a reactor, some microorganisms are transported during a defined time interval several times to the irradiation zone, while others only once, and others not at all. So the inactivation rate, based on the chemically determined dose-rate, increases with mixing. The faster the microorganism inactivation proceeds, the shorter the necessary irradiation time, and the smaller the required effective dose has to be. Therefore, protein or other biological activity will be retained at a higher mixing efficiency.

Biodosimetric inactivation is measured by a microorganism titer before and after UV-irradiation. For example, this may be accomplished by counting the number of residual colonies of viable bacteria, or lysed bacteria plaques which correspond to the number of bacteriophages still alive. The titer of viable microorganisms as colony- or as plaque-forming units (cfu and pfu, resp.) is then calculated as $\log_{10}$ ((cfu or pfu)$\times 10^{dilution\ factor}$) per mL of diluted sample volume titrated on a petri dish.

Biodosimetry demonstrates that different protein solutions have been irradiated with the same effective dose at the same mixing efficiency when the phage inactivation rate (log [number phages inactivated]/effective UV dose) is similar. Biodosimetry is suitable for validation of different samples if these do not contain any substances toxic or inhibitory to the microorganisms or their hosts. Accordingly, biodosimetry can used with virtually all biological fluids.

Preferably intensity measurements are made continuously and any UV source may be shut down: after having reached an irradiating dose as predetermined by chemical dosimetry. The radiometric lamp dose increases in a linear ratio with the absorption of the protein solution. Lamps operating at a lower intensity will take more irradiation time to reach the radiometric target lamp dose.

Any given UV-dose may be measured in mJ/cm$^2$. Irradiating dose is the total lamp power over time. However, only part of this irradiating dose will become effective as measured by chemical dosimetry and inactivation of bacteriophages. For example, a 30 L batch reactor may require an irradiating lamp dose that is about 1000 times higher than the effective dose. As shown above, determination of an effective dose by chemical dosimetry also yields irradiation time. In the case of slightly changing lamp power, the irradiation time may be replaced by the irradiating dose. This is determined by recording lamp intensity during the irradiation runs of the model dosimetry solutions. While the virucidally effective target dose is determined, intensity counts are summed up over the irradiation time to obtain the radiometric target lamp dose corresponding to the effective dose. Control of the process by irradiating lamp dose can compensate for changes in lamp power and can increase the accuracy of the instant method.

In addition to light treatment, protective additives may also be used to reduce damage and loss of biological activity. Various protective additives are known in the art such as vitamin E for protecting cells against damage, ascorbate to protect against loss of functional activity of plasma constituents, and quenchers of free radicals and active forms of oxygen such as histidine, rutin, quercetin and other flavonoids, and other stabilizers such as sugars such as mannitol and amino acids for reducing loss of functional activity of blood components. It is also known from the state-of-the-art that the removal of oxygen dissolved in the solution, e.g. by evacuation, prior to the irradiation and the replacement of air during the irradiation by an inert gas, e.g. by nitrogen, may exert a beneficial effect on substances of interest, because the generation of singlet oxygen would require dissolved oxygen.

In one embodiment, the instant methods for inactivation and dose determination are used in combination with various other known methods for sterilization of fluids and viral inactivation. Various methods are well known in the art and include conventional wet heat treatment or pasteurization comprising incubation of fluid at an elevated temperature for a given period of time with or without stabilizers, as generally used for albumin. Alternatively, dry heat treatment comprising incubation of freeze dried fluid components at an elevated temperature for a given period of time as used for components such as Factor VIII. Another method includes ultra-filtration and solvent detergent treatment wherein the fluid is intimately admixed with a solvent detergent system such as 1% tri(n-butyl)phosphate (TNBP) and 1% Triton X-100 or Tween 80, and incubated together therewith for a given period of time followed by removal of the solvent detergent system, conveniently by hydrophobic chromatography. Details of solvent detergent treatments are described in WO 94/28120; and U.S. Pat. Nos. 4,946,648; 4,481,189; and 4,540,573.

In another embodiment, a UV irradiation of the instant invention is used in combination with a solvent detergent treatment. One feature of solvent detergent treatment is that it may give rise to significant increases in the absorbance of fluids treated thereby, and in this connection the capability of the method of the present invention to achieve effective viral inactivation in fluids with relatively high absorbance is a particular advantage.

In another embodiment, methods for UV inactivation of microorganisms according to the present invention is performed together with at least one other microorganism inactivating procedure. In this regard, different types of virus can have different susceptibilities to various treatments, and it is often necessary to use a combination of different treatments to ensure inactivation of all the different viruses present. A particular benefit of the irradiation treatment of the present invention is that certain types of virus which are resistant to other readily available treatments, are susceptible to irradiation treatment.

In another embodiment, the validation method based on chemical dosimetry and biodosimetry may be used to optimize the mixing parameters in a UV irradiation reactor, by achieving a maximum logarithmic titer reduction of an added microorganism at a defined dose as determined by chemical dosimetry.

In another embodiment, the invention provides a batch irradiation reactor comprising an upright irradiation vessel with a wall transparent to a photoinactivating light wavelength, a stirrer within the vessel capable of mixing a volume of material placed within the vessel by moving fractions of the volume to and away from an irradiation zone, one or more light sources thermostated to emit a constant radiance of the photoinactivating wavelengths into the irradiation vessel, and an electronic monitoring device with a sensor sensitive to the photoinactivating wavelengths. Preferably, the light sources are equipped with reflectors to reflect light onto the transparent wall of the irradiation vessel, and the light sources are switchable individually. A monitoring radiometer signals emitted by the sensor are summed up to a target value by means of a mechanical, electronic or computer-software-controlled counter. One or more light sources may be turned off automatically when energy from the photoinactivating wavelengths has reached the target value. The light sources may be mounted externally and may be thermostated by a cooling liquid. The stirrer may be a stacked impeller stirrer with near-wall wiper blades.

Since enzymatic denaturation is temperature-dependent and suppressed at lower temperatures, and photochemical reactions such as nucleic acid inactivation and protein photodenaturation are temperature-independent between 0 and ~50° C. (Engelhard and Eikenberg 1955), a batch reactor layout with external separate lamps allows one to irradiate the pre-cooled fluid in a short time without relevant temperature increase from the lamps operated at optimum temperature for maximum UV-C-radiance.

Figure 7:
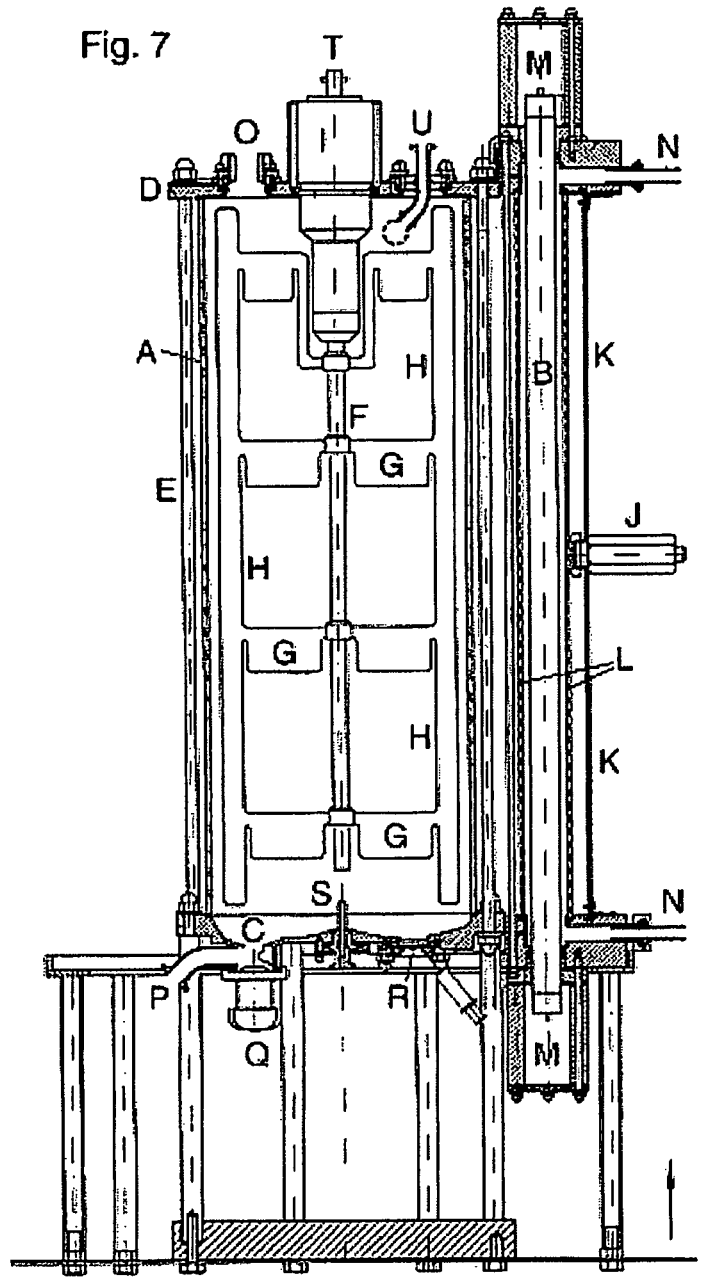
FIG. 7 depicts the longitudinal cross-section of an exemplary reactor of the instant invention.
Figure 8:
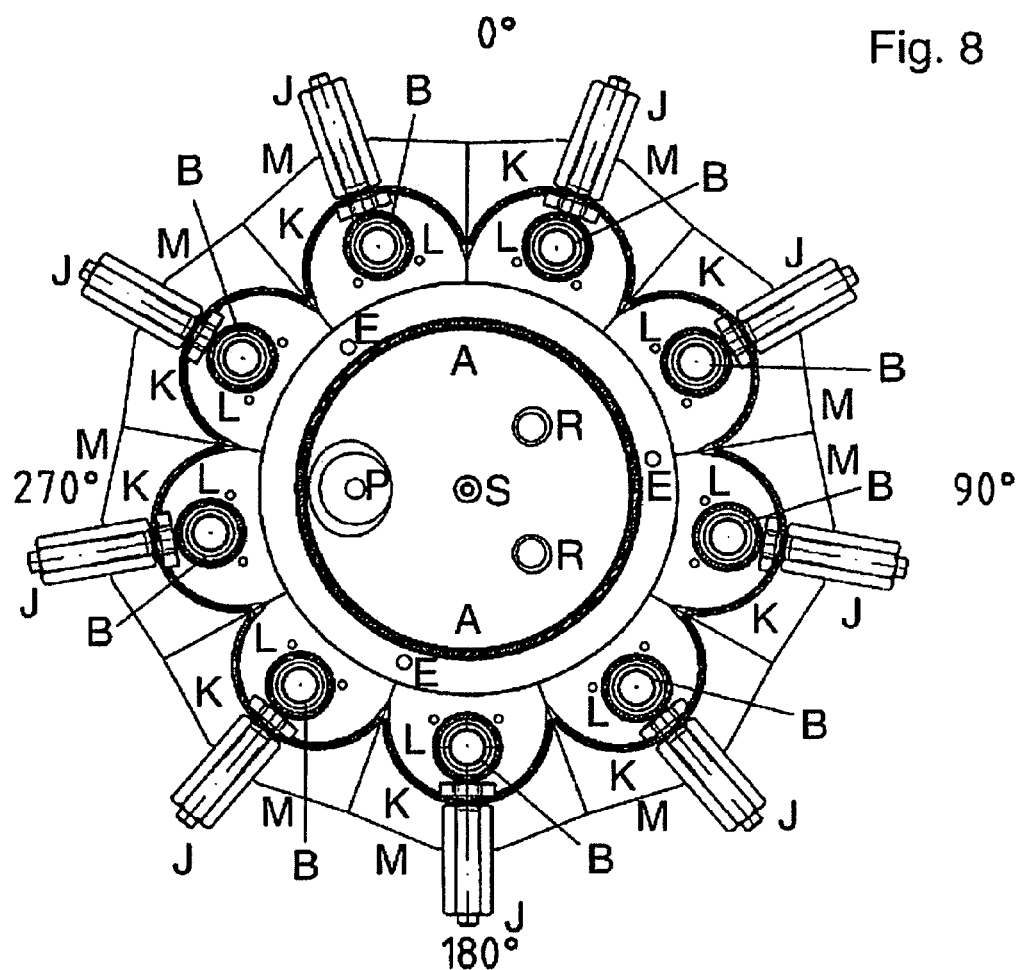
FIG. 8 depicts the transversal cross-section of an exemplary reactor of the instant invention.
Figure 9:
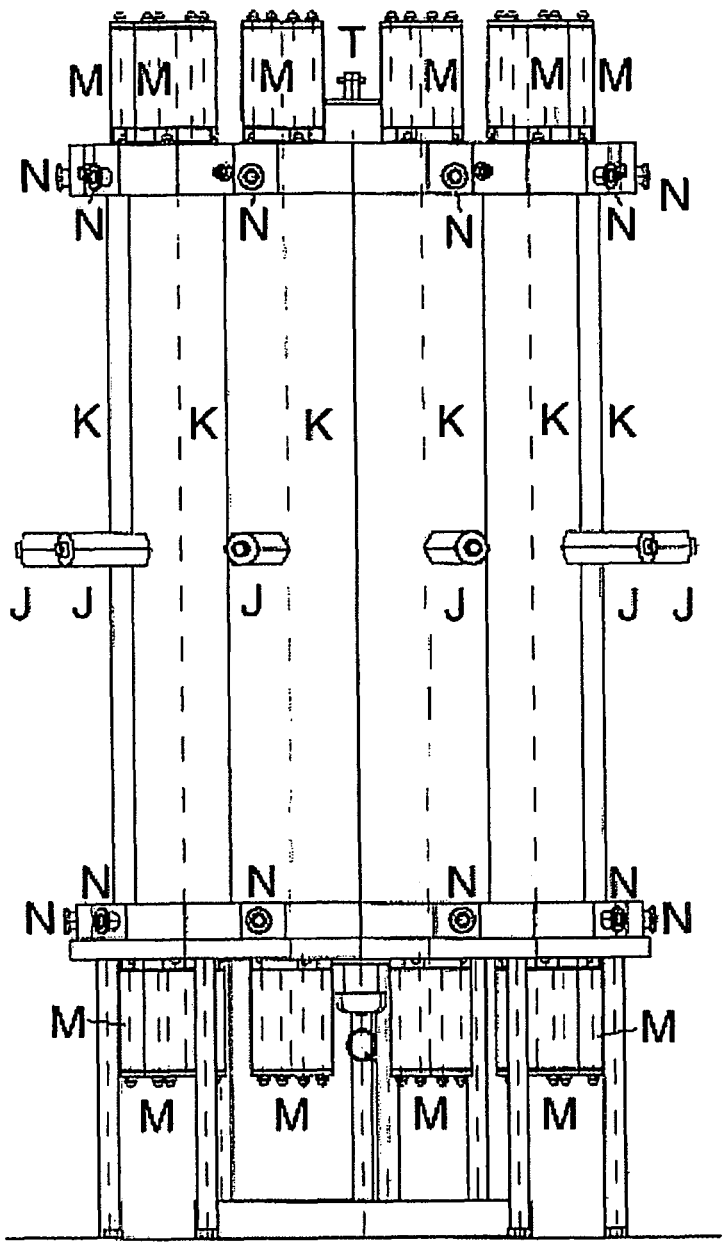
FIG. 9 depicts the side view of an exemplary reactor of the instant invention.

Preferred reactors of the instant invention is shown in FIGS. 7-9, which comprise an upright cylindrical tube (A) made of a material sufficiently transparent to the photoinactivating light wavelengths applied. The tube (A) is surrounded by light sources (B) emitting light of the photoinactivating wavelengths. The light sources are preferably tubular light sources, more preferably gas discharge tubes filled with mercury vapor or xenon gas, which may be lined with a fluorescent inner coating to convert the primary emission to light of longer wavelengths.

The tube (A) is sealed at its lower end with an outward-curved bottom (C) to ensure a smooth flow of the contained fluid without any dead volumes, and at its upper end with a top lid (D). The distance rods (E) between the bottom (C) and the top lid (D) support the sealing of the tube. The fluid is stirred with a stirrer (F) mounted on the top lid which generates sufficient mixing with stacked impeller blades (G) and optional additional longitudinal scraper blades (H). The stirrer is rotated by a stirring motor (I).

Each lamp is monitored by its own lamp sensor (J) connected to an intensity monitor, recorder, and very preferably, the light dose counter. The lamp's light output may be enhanced by a reflector (K) consisting of a material of sufficient reflectance focusing the light onto the cylinder. Preferably, the lamp's light output is controlled by its operating temperature, preferably by a stream of light-transparent thermostating liquid contained in the space between the lamp and a light-transparent envelope tube (L). The lamp mounts (M) seal the flow path of the thermostating liquid, flowing between the inlet (N)/outlet (N), from the lamp's power connectors.

The product is injected into the reactor using an insertable flexible tube or a rigid tubular lance via the inlet (O) in the top lid, and drained after the irradiation via the outlet (P)

equipped with a valve (O) to avoid cross-contamination of the treated with the untreated fluid.

An additional sampling port (R) enables the drawing of in-process samples, preferably with a hypodermic needle of an injection syringe through a rubber septum. A temperature sensor (S) monitors the fluid's temperature. A coupler (T) connects the stirring motor (I) to a revolution controller to ensure effective mixing. An insertable spray ballhead (U) enables the cleaning in place of the reactor.

In another embodiment the invention provides a device for calibration comprising: a light source, a light exit aperture allowing the light to radiate into an collimator aperture, a shutter, and a cuvette slot mounted in a thermostated housing with a light entrance aperture allowing light to radiate onto the cuvette or optical cell containing the dosimeter solution. A preferably thermostated mount may be provided for the attachment of radiometer sensors, wherein light radiates simultaneously from the light source both through the shutter onto the cuvette and through the aperture onto the entrance window of the sensor, to monitor the light source through the calibration process, or to check the time-constant properties of such a sensor by comparison with an actinometer solution according to the state-of-the-art contained in the simultaneously exposed said cuvette or optical cell. Very preferably the shutter is driven by an accurate timer to achieve an exact and reproducible exposure time of the cuvette or optical cell. A preferred calibration device is shown in FIG. 10. The preferably tubular lamp (T) mounted in a housing (U) is preferably thermostated or current-stabilized, very preferably both thermostated and current-stabilized, to achieve a constant light radiance through the calibration process. As indicated in FIG. 10, the thermostatization is preferably achieved by a light-transparent liquid flowing past the lamp. The light, indicated by the arrows pointing away from the lamp, is radiating through an aperture (V) past the time-controlled opened shutter (W) onto the cuvette inserted together with its distance adapter, if the cuvette is thinner than the maximum space in the holder, into the said cuvette holder (X), which is preferably thermostated. The cuvette containing the actinometry or the model dosimetry solution is accurately and precisely exposed during the opening of the shutter. An optional aperture (Y) located on a place other than that for the aperture (V), but preferably in a way so that the light radiates spatially similar from the lamp into both apertures (V and Y), may accommodate an electronic sensor (Z), such as preferably, but not limited to, one of the sensors used for the reactor radiometry, providing an accurate method to recalibrate the sensor based on the ratio of the intensities preferably measured simultaneously by actinometry in the cuvette holder (X) and by radiometry with the sensor (Z). The sensor (Z) may also be used for the monitoring and recording of the lamp intensity during the calibration exposure, and for the subsequent intensity correction, if the lamp intensity changed during this calibration exposure.

The following examples illustrate embodiments of the invention; but do not limit the scope of the invention in any manner.

Example 1

Absorption Coefficients of the Iodide/Iodate Actinometer Solution at High Dilution, Dosimetric Response of the Iodide/Iodate Actinometer Solutions, and Stabilization of the UV-C Generated Tri-Iodide by Polyvinylpyrrolidone A solution containing 0.24 M KI and 0.04 M in 0.01 M borate buffer, pH=9.25, was diluted 0.2-, 0.4-, 0.6- and 0.8- fold with 0.01 M borate buffer and the absorption measured in a 0.1 mm cuvette. FIG. 1 shows that the absorption coefficient depends in a linear ratio ($a_{253.7}$=69/cm×dilution factor) on the concentration.

Figure 2:
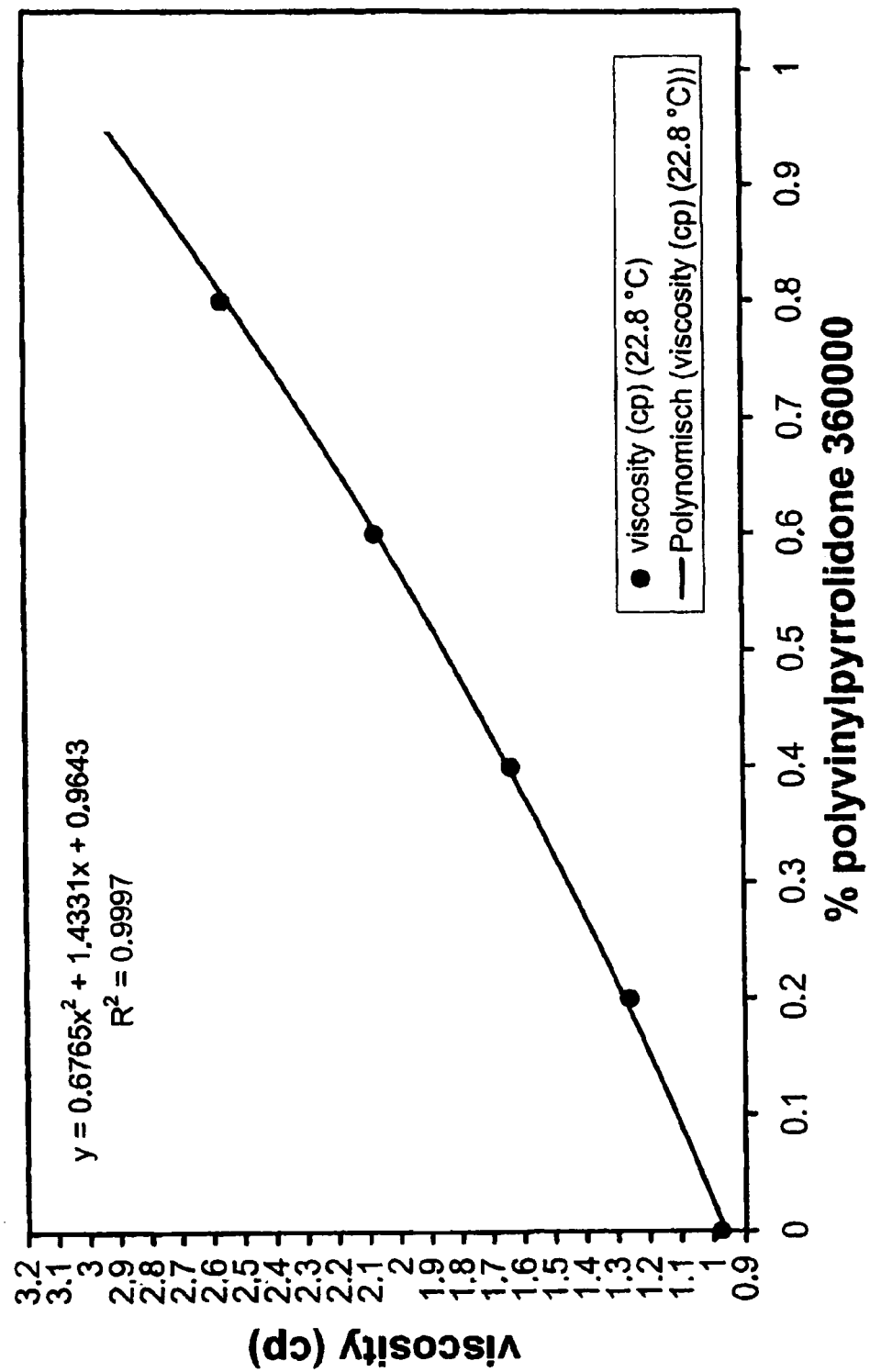
FIG. 2 depicts the non-linear relationship between increase in viscosity and polyvinylpyrrolidone concentration.

A solution containing 10 g polyvinylpyrrolidone K90 (PVP K90; average molar mass 360000 Da) in 1 L 0.01 M borate buffer was diluted 0.2-, 0.4-, 0.6-, 0.8-fold and the viscosity of the dilutions and the buffer were measured in a Schott 0.40 mm Ubbelohde capillary viscosimeter thermostated at 22.8° C. It can be seen from FIG. 2 that the viscosity increases with the concentration in a non-linear ratio.

Figure 3:
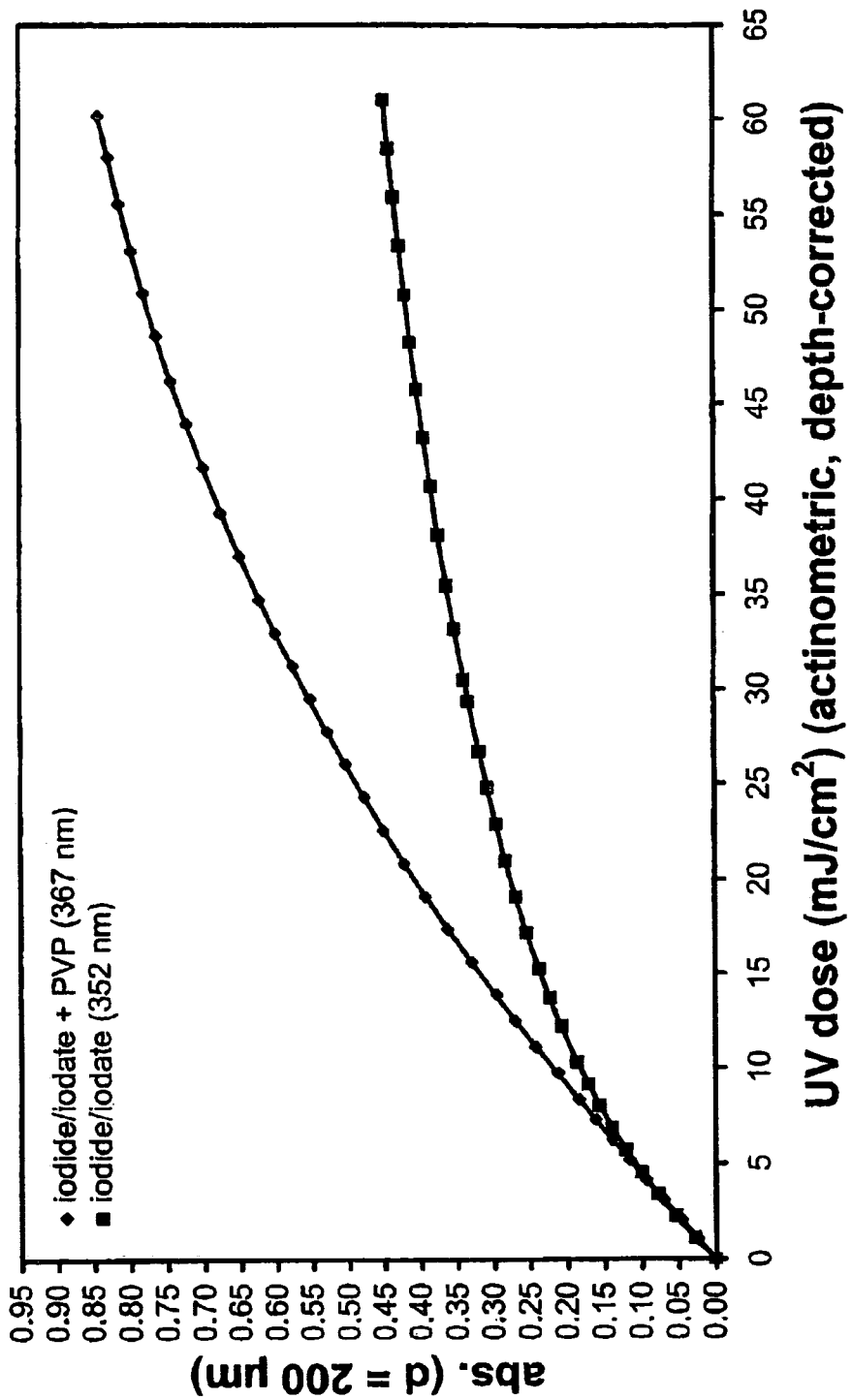
FIG. 3 depicts the increase in absorbance with applied surface dose, and increase in sensitivity with $KI/KIO_3$ concentration.

Dilutions of the stock solution containing 0.24 M KI and 0.04 M in 0.01 M borate buffer, pH=9.25, were prepared to a defined absorption at 253.7 nm of 6.1/cm (0.0212 M KI+0.0035 M $KIO_3$+0.95 g PVP K90/L; for prothrombin complex eluate from DEAE sephadex anion exchange gel (Brummelhuis 1980)) and 16/cm (0.06 M KI+0.01 M $KIO_3$+ 6.25 g PVP K90/L; for a 2.5% (w/v) fibrinogen solution), and filled into the 0.2 mm cuvettes. The thin-layer calibration was done by placing the cuvette filled with the dosimetry solution for a defined time under a CAMAG TLC lamp with a known irradiance (measured with the Rahn actinometer) at the cuvette position. The absorbance was measured at 367 nm. From FIG. 3 it can be seen that the absorbance increases with the applied surface dose, and that the sensitivity increases with the KI/$KIO_3$ concentration.

Figure 4:
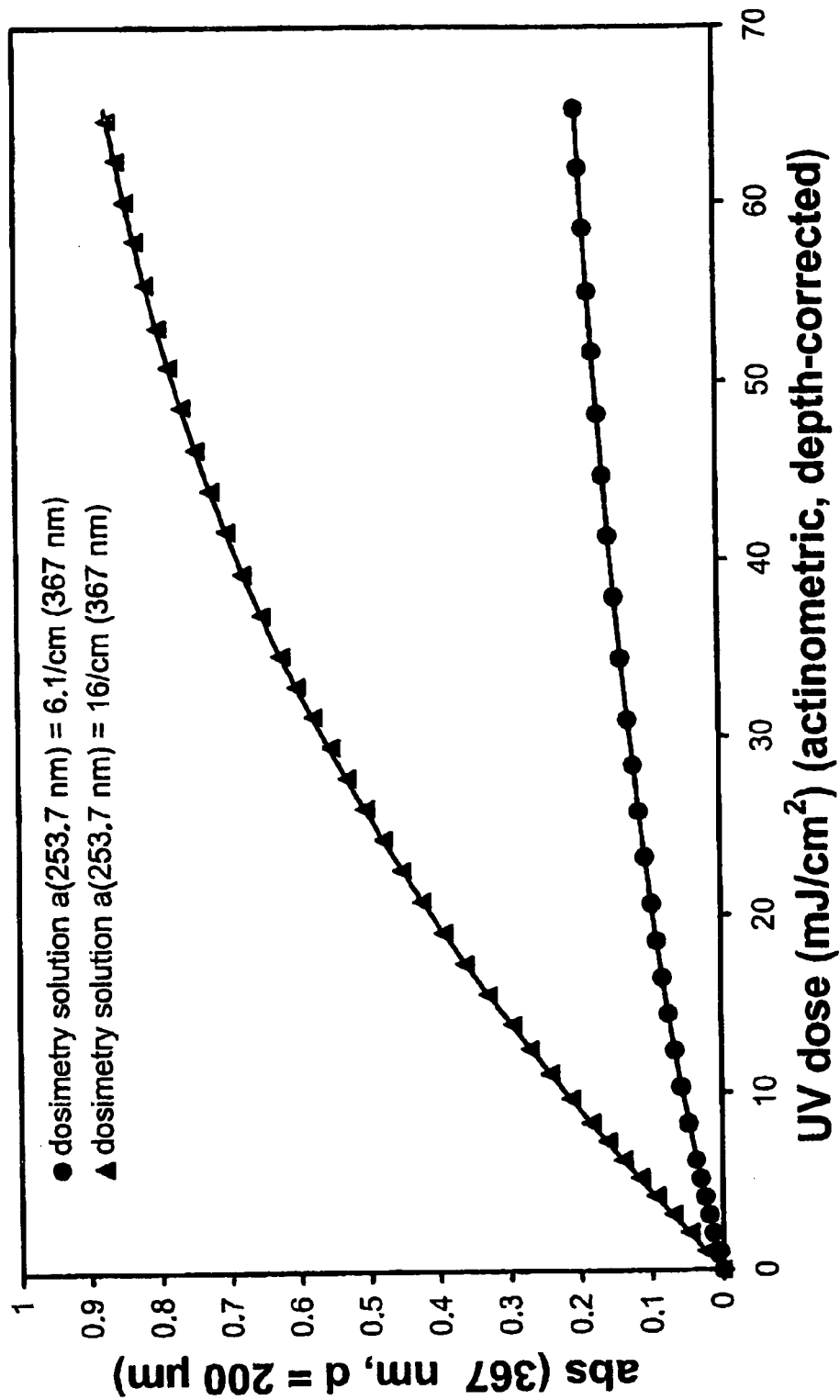
FIG. 4 depicts the sensitivity improvement with PVP.

A dosimetry solution containing 0.06 M KI and 0.01 M $KIO_3$ in 0.01 M borate buffer, pH=9.25, with an absorption coefficient of $a_{253.7}$=16/cm, and a solution with the same KI and $KIO_3$ concentration and 6.25 g polyvinylpyrrolidone (PVP) K 90/L were prepared. The thin-layer calibration was done by placing a 0.2 mm cuvette filled with the dosimetry solution for a defined time under the CAMAG TLC lamp as described above. The absorbance was measured at 352 nm (KI+$KIO_3$ only) or 367 nm (KI+$KIO_3$+PVP). From FIG. 4 it can be seen that PVP improves the sensitivity of the method.

Example 2

Determination of the Irradiation Time in a Batch Photoreactor with Fixed Geometry with Actinometric Dosimetry Solutions Dosimetry solutions with decadic absorption coefficients $a_{253.7}$ of 2.1/cm (0.0072 M KI+0.0012 M $KIO_3$+0.5 g PVP K90/L, for FVIII concentrate), 6.1/cm (see Example 1), 10/cm (0.0346 M KI+0.0058 M $KIO_3$+1.21 g PVP K90/L; for a 2% (w/v) immunoglobulin G solution), and 16/cm (see Example 1) were prepared and calibration plots recorded as described in Example 1. A quartz test tube 4 cm in diameter was filled with 100 mL dosimetry solution, stirred with a magnetic stirrer bar on a magnetic stirrer, and irradiated between 2 low-pressure mercury vapor lamps equipped with polished stainless steel reflectors. At predefined intervals, samples were drawn and filled into the 0.2 mm cuvettes for spectrophotometric measurement, and the dose was read out from the calibration plot. The dose-rate was then calculated as (mJ/$cm^2$)/min, and the inverse dose rate, i.e. the specific irradiation time per unit dose as min/(mJ/$cm^2$). The constant $k_1$ for the relation between the absorption coefficient and the (specific) irradiation time can be calculated:

| $t = k_1 \times a$ | | | | |
|---|---|---|---|---|
| | solution $a_{253.7}=$ | | | |
| | 2.1/cm | 6.1/cm | 10/cm | 16/cm |
| dose-rate ((mJ/cm$^2$)/min) | 14.40 | 3.68 | 2.71 | 1.56 |
| specific irradiation time (min/(mJ/cm$^2$)) | 0.0694 | 0.2714 | 0.3688 | 0.6410 |
| constant $k_1$ (average = 0.0386) | 0.0330 | 0.0445 | 0.0369 | 0.0401 |

By calculation of the linear regression of the specific irradiation-time depending on the absorption coefficient a linear correlation of $R^2=0.989$ is obtained. This result demonstrates that the dosimetry based on absorption- and viscosity-matching model solutions with thin-film calibration is suitable for the validation of stirred batch photoreactors.

Example 3

Inactivation of MMV and Phi-X 174 in Thin Layer- and Batch Irradiation

MMV stock solution from cell culture supernatant (~10$^8$ tissue-culture infectious doses (TCID$_{50}$)/mL) and bacteriophage Phi-X 174 lysate (~1×10$^9$ plaque-forming units (PFU)/mL) from propagation in *Escherichia coli* were diluted in 20 mM phosphate-buffered 0.15 M NaCl (phosphate-buffered saline, PBS) and 2.5 mL were irradiated with different UV-C doses in 32 mm polystyrene petri dishes shaken horizontally under a CAMAG TLC lamp. The irradiance at the sample surface distance was determined with a Dr. Groebel RM21-radiometer with a daylight-blind UV-C sensor, and the self-absorbance of the solution measured in a spectrophotometer to correct for the effective fluence (UV dose) (Morowitz 1950). MMV and Phi-X 174 titers were determined by titration on host cell culture and host bacteria respectively.

| UV dose (mJ/cm$^2$) | $\log_{10}$ pfu Phi-X 174/mL | UV dose (mJ/cm$^2$) | $\log_{10}$ TCID$_{50}$ MMV/mL |
|---|---|---|---|
| 0.00 | 6.41 | 0 | 6.54 |
| 2.25 | 5.79 | 2 | 5.31 |
| 4.50 | 4.37 | 4 | 4.42 |
| 6.75 | 3.46 | 6 | 3.52 |
| 9.00 | 2.36 | 8 | 2.93 |
| 11.25 | 1.35 | 10 | 2.37 |
| | | 12 | 1.44 |
| inactivation rate | −0.468 ($\log_{10}$(PFU/mL))/ (mJ/cm$^2$) | | −0.405 $\log_{10}$(TCID$_{50}$/ mL))/(mJ/cm$^2$) |

Into a 100 mL quartz bottle with a 4 cm stirrer bar 80 mL MMV- or Phi-X 174-spiked protein solution (prothrombin complex DEAE sephadex eluate, $\alpha_{253.7}=6.9$/cm) were filled, placed on a magnetic stirrer, stirred at ~250 rpm, and Irradiated from the side with a CAMAG TLC lamp. The calibration was done with a model solution ($\alpha_{253.7}=6.9$/cm) as described in example 2. Samples for virus or bacteriophage titration were drawn at time intervals calculated after the measured dose-rate and titrated to determine the titer of surviving infectious virus or bacteriophage.

| UV dose (mJ/cm$^2$) | $\log_{10}$(pfu Phi-X 174/mL) | UV dose (mJ/cm$^2$) | $\log_{50}$(TCID$_{50}$ MMV/mL) |
|---|---|---|---|
| 0.00 | 7.27 | 0.00 | 6.77 |
| 1.69 | 5.96 | 6.86 | 3.46 |
| 3.37 | 5.52 | 13.70 | 0.61 |
| 5.06 | 4.78 | | |
| 6.74 | 3.95 | | |
| 8.42 | 3.11 | | |
| 10.10 | 2.39 | | |
| 11.79 | 1.28 | | |
| Inactivation rate | ($\log_{10}$(pfu/mL))/ (mJ/cm$^2$) −0.480 | Inactivation rate | ($\log_{10}$(TCID$_{50}$mL))/ (mJ/cm$^2$) −0.425 |

From the inactivation rates of Phi-X 174 and MMV it can be deduced that their sensitivity to UV-C light at 253.7 nm is similar. Therefore Phi-X 174 was used as a biodosimeter. It can also be seen that the inactivation rates for the UV-C-absorbing liquid in the batch-stirred device are almost the same due to efficient method of mixing ensuring the transport of the microorganisms to the irradiation zone.

Example 4

Use of Dosimetry and Biodosimetry for the Optimization of a Stirred Batch-Reactor A cylindrical quartz vessel (7 cm inner diameter, 3 mm wall thickness, 13 cm in height) equipped with a stacked impeller stirrer (3 impellers, adjustable stirring speed) was illuminated from the side with two low-pressure mercury lamps, each mounted in an envelope of two concentric quartz tubes and equipped with a stainless steel reflector behind. Cooling water from a thermostat was pumped through the lamp envelope to keep the lamp temperature and the UV-C-output constant.

The stirring rate was adjusted to 60 rotations per minute (rpm) (slow stirring), 150 rpm (medium-fast stirring), and 240 rpm (fast stirring). The UV dose-rate for the irradiation of 450 mL absorption- and viscosity-matching model solution for bacteriophage-spiked prothrombin complex eluate ($a_{253.7}=8.0$/cm, $\eta=1.15$ cp, 27.83 mM KI, 4.64 mM KIO$_3$, 1.3 g PVP K90/L in 0.1 M borate buffer, pH=9.25) was determined as described in Example 2. It was discovered that higher borate concentrations (≥0.1 M) than given in the literature (0.01 M) effect a higher sensitivity and a better stability of the dosimeter solution. The bacteriophage-spiked prothrombin complex eluate was irradiated and the bacteriophage inactivation determined as described in Example 3. As an additional parameter, the activity of coagulation factor X (FX) was measured using the amidolytic assay for doses of 0, 10, 15, 20, 25, 50, 75, and 100 mJ/cm$^2$.

| | stirring rate | | |
|---|---|---|---|
| | 60 rpm | 150 rpm | 240 rpm |
| UV-C dose-rate (dosimetry) ((mJ/cm$^2$)/min) | 1.770 | 1.794 | 1.799 |
| Phi-X 174 inactivation rate (biodosimetry) ($\log_{10}$(pfu/mL))/(mJ/cm$^2$) | −0.277 | −0.399 | −0.460 |
| UV-C dose required to Inactivate 5 $\log_{10}$(pfu/mL) | 18.05 | 12.53 | 10.87 |
| FX inactivation rate (U FX/mL)/(mJ/cm$^2$) | −0.0054 | −0.0048 | −0.0051 |
| FX inactivation at 20 mJ/cm$^2$ (% unirradiated) | 88 | 88 | 89 |

From this experiment, it can be seen that the optimization of a virus inactivation batch photoreactor can be done by model solution dosimetry and biodosimetry, because both methods of validation give information about the effectiveness of mixing. It is also evident that at the highest stirring rate possible for a protein solution (to avoid the generation of foam), the fastest pathogen inactivation will be achieved. The benefit of such an optimization is that with the most effective mixing, the safety margin for the virus inactivation at a target dose e.g. of 20 mJ/cm$^2$ is the highest, or the target dose can be reduced to conserve additional biological activity of the protein.

Example 5

Validation and Process Monitoring for the Batch Irradiation of Prothrombin Complex Eluate Using Chemical Dosimetry, Biodosimetry, and Radiometry A virus inactivation photoreactor having a cylindrical quartz tube (25 cm inner diameter, 5 mm wall thickness, 75 cm length), a flat top lid and a curved bottom with sampling ports, and a stacked impeller stirrer with three three-blade impellers and a wiper blade at each outer blade edge, was surrounded with 10 water-thermostated UV-C-lamps (Philips TUV 55W HO), each monitored with a DR. Groebel UVC-SE radiometer sensor. The maximum capacity of this reactor is 30 L. The lamp power was recorded using a radiometer sensor for each lamp on a chart recorder, and the relative lamp power normalized to the first run set as 100%.

29.5 L prothrombin complex eluate were spiked with 0.5 L Phi X-174 lysate (~$4\times10^9$ pfu/mL) from *E. coli*. The resulting solution had an absorption coefficient of $a_{253.7}$=6.0/cm. The reactor dose-rate was determined prior to the virus inactivation experiments with an absorption- and viscosity-matching model solution as described in example 2 containing 20.87 mM KI, 3.48 mM KIO$_3$, and 1.304 g PVP K90/L in 0.1 M borate, pH=9.25, with a dose rate of 1.3435 (mJ/cm$^2$)/min and a lamp dose rate relative to the first bacteriophage irradiation run of 98.5%. An irradiation time of 14 min had been determined for a target dose of 20 mJ/cm$^2$, and a constant dose-rate was assumed. To demonstrate the effect of the lamp power as an error source, the lamp temperature was lowered for the third run from 28° C. to 24.5° C. to reduce the lamp power to about 90% of the maximum. The inactivation rate of Phi-X 174 (based on the assumed constant dose rate) was determined as described in example 3 and expressed as (log (pfu/mL))/(mJ/cm$^2$).

|  | run No. 1 (=100%) | run No. 2 | run No. 3 |
|---|---|---|---|
| lamp power | 100% | 101.4% | 89.3% |
| Phi-X 174 inactivation rate k (uncorrected) | −0.4272 | −0.4331 | −0.3742 |
| Phi-X 174 inactivation rate, corrected for lamp power | −0.4272 | −0.4275 | −0.4190 |

From Example 5 it can be seen that the lamp power is a parameter of the batch irradiation process, and that both dosimetric dose-rates and biodosimetric inactivation rates have to be normalized to the lamp power.

Example 6

Process Design for the Batch Irradiation of Protein Solutions Based on a Radiometric Target Dose Determined by Dosimetry and Radiometry The photoreactor described in example 4 was validated for the dose-rates and irradiation times for the irradiation of model solutions with absorption coefficient of 6.0/cm, 7.0/cm, 8.0/cm, 9.0/cm and 10.0/cm. A sample volume of 450 mL was stirred at 200 rpm. The lamps turned on and the dose rate was determined by the measurement of model solution samples drawn at 3, 6, 9, 12, 15, 18, 21, and 24 min. The lamp intensity was monitored and recorded by a dual-head radiometer connected to a computer.

Figure 5:
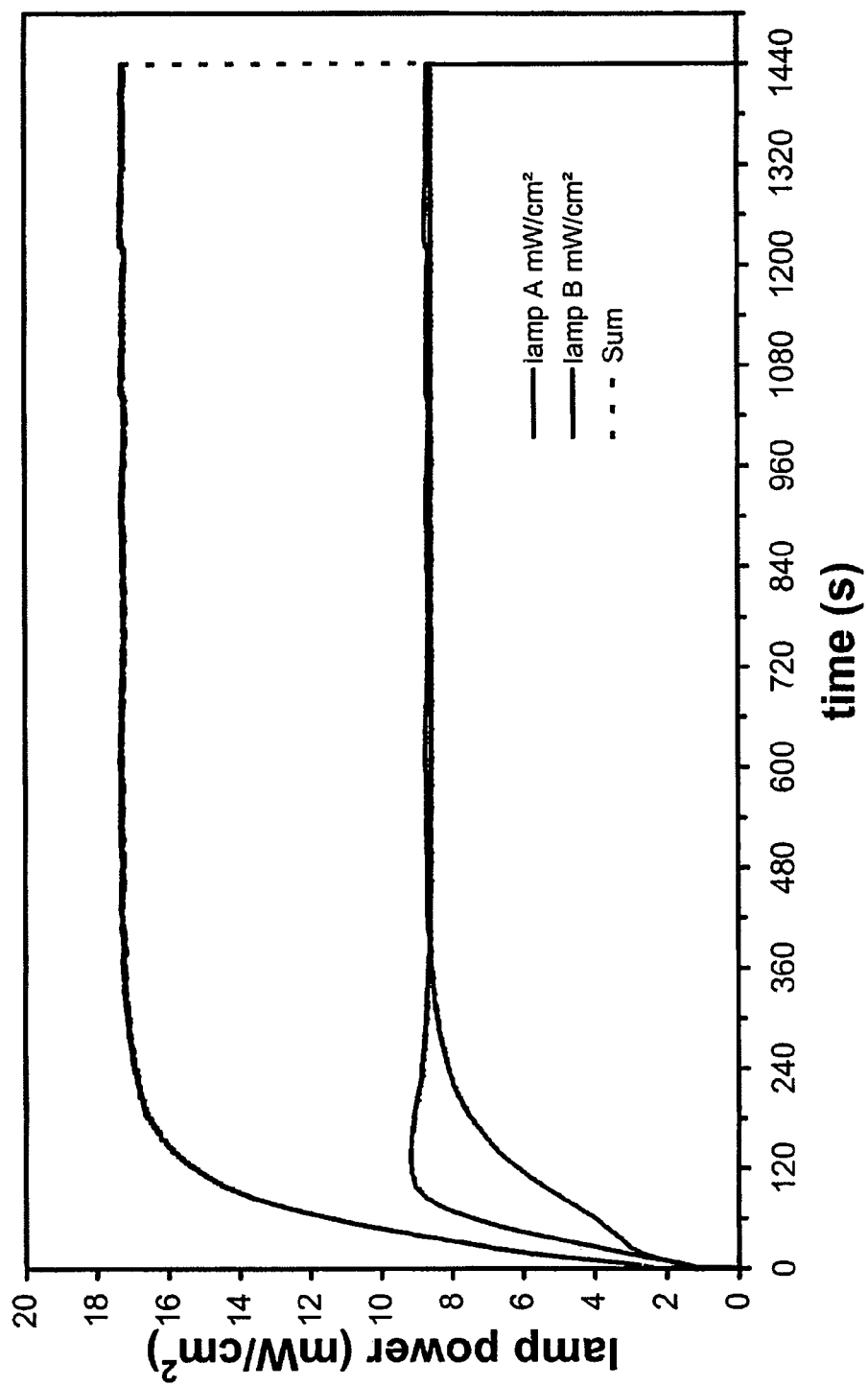
FIG. 5 depicts the lamp intensity changes.
Figure 6:
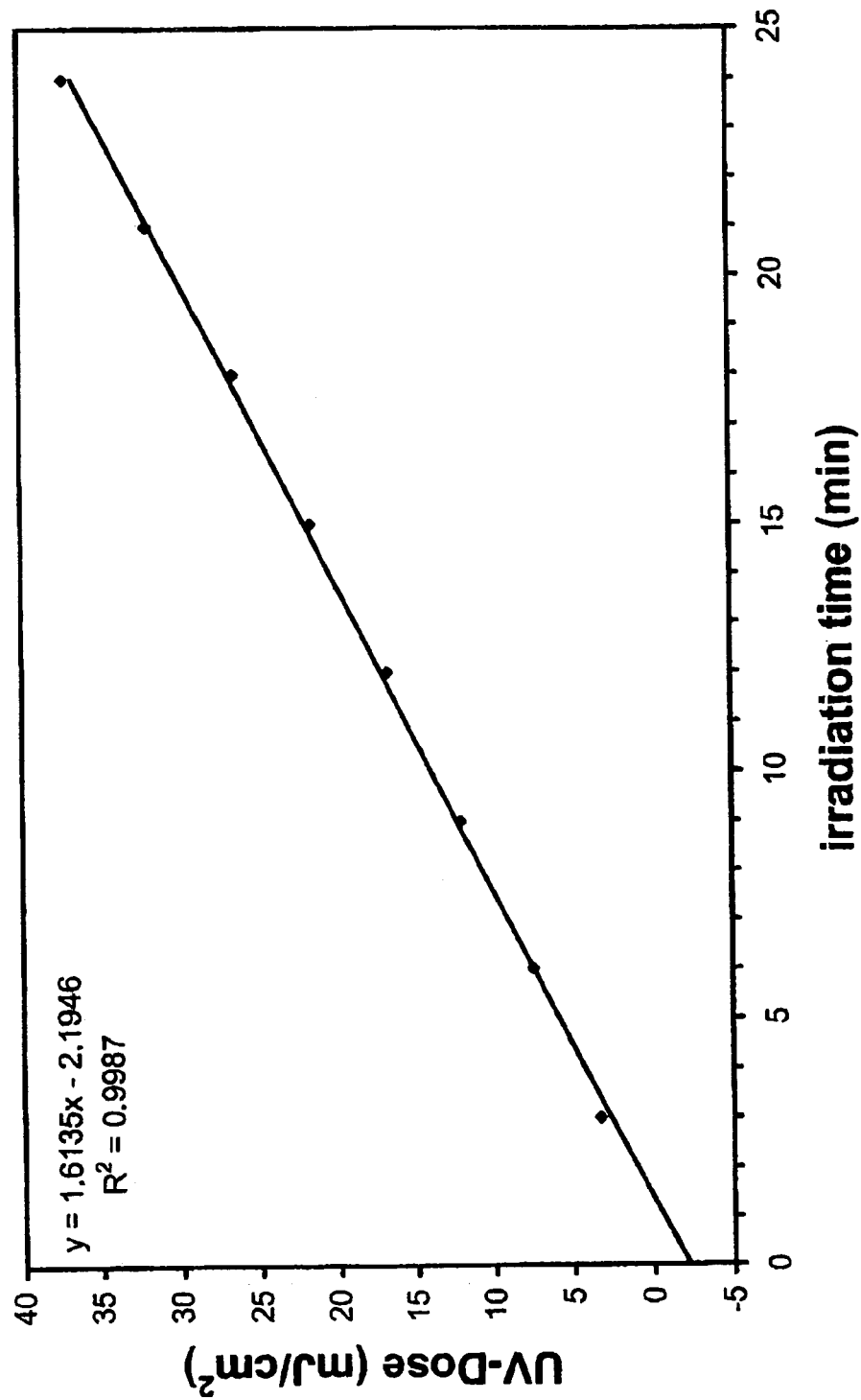
FIG. 6 depicts the dose-increase with error expressed as a y-axis constant.

FIG. 5 shows that the lamp intensity reaches its maximum 3 minutes after being turned on, and that the dose applied during the first 3 minutes is lower than the constant dose-increase applied in the following 3 minute time-intervals. FIG. 6 shows the corresponding dose-increase with the error expressed as the y-axis constant below zero. Therefore, the y-axis constant of the dose-rate equation was added to the target dose (20 mJ/cm$^2$) to obtain the corrected augmented target dose, the irradiation time calculated by dividing the augmented target dose by the dose-rate, and the lamp intensities measured in 1 second intervals (mW/cm$^2$) summed up over the irradiation time to obtain a target radiometric lamp dose (mJ/cm$^2$) depending on the absorption coefficient. The constant $k_2$ can be calculated:

| $Q = k_2 \times a$ | | | | | |
|---|---|---|---|---|---|
| | absorption coefficient $a_{263.7}$ | | | | |
| | 6.0/cm | 7.0/cm | 8.0/cm | 9.0/cm | 10.0/cm |
| target radiometric lamp dose Q (mJ/cm$^2$) | 11879 | 13674 | 16038 | 18660 | 21102 |
| constant $k_2$ (average = 2024) | 1980 | 1953 | 2004 | 2073 | 2110 |

From the table in Example 6 it can be seen that the radiometric target lamp dose increases with the absorption coefficient in a linear ratio ($R^2$=0.996).

Example 7

Dosimetric Compensation for the UV-C Absorbing Effect of Ascorbate Tested as Protectant from Photodenaturation To FEIBA DEAE sephadex G50 eluate (18.2 mg protein/mL), sodium ascorbate was added to a concentration of 1 mmol/L. The absorption coefficient $a_{253.7}$ of the ascorbate-added FEIBA eluate was 16/cm compared to 7.3/cm for the native eluate.

For chemical dosimetry, model solutions containing 0.0254 M KI, 0.0042 M KIO$_3$ and 1.61 g PVP K90/L 0.1 M borate buffer, pH=9.25 (for $a_{253.7}$=7.3 cm) and 0.06 M KI, 0.01 M KIO$_3$ and 1.61 g PVP K90/L 0.1 M borate buffer, pH=9.25 (for $a_{253.7}$=16/cm) were prepared, calibration plots were recorded with 0.2 mm thin-layer cuvettes, and 110 mL were irradiated in the batch photoreactor described in example 2 with 1 lamp (for $a_{253.7}$=7.3/cm with a dose rate of 1.41 (mJ/cm$^2$)/min) and 2 lamps (for $a_{253.7}$=16/cm with a dose-rate of 1.33 (mJ/cm$^2$)/min).

110 mL of both the native FEIBA eluate and the ascorbate-added FEIBA eluate were irradiated at the respective dose-rate, and samples were drawn at 5; 10; 15; 20; 25; 30; and 35 mJ/cm². Factor X (FX) activity was determined as in Example 4.

| UV dose (mJ/cm²) | FX activity (% unirradiated) FEIBA native | FX activity (% unirradiated) FEIBA + 1 mM Na-ascorbate |
|---|---|---|
| 0 (unirradiated) | 100 | 100 |
| 5 | 94 | 101 |
| 10 | 95 | 93 |
| 15 | 86 | 98 |
| 20 | 89 | 91 |
| 25 | 84 | 85 |
| 30 | 85 | 89 |
| 35 | 84 | 88 |
| FX Inactivation rate (U/(mJ/cm²)) | −0.0045 ($R^2 = 0.7886$) | −0.0043 ($R^2 = 0.7727$) |

From the table in Example 7, it can be seen that there is no relevant difference in the FX inactivation rate (U FX/(mJ/cm²)) between the native and the ascorbate-added FEIBA eluate. Therefore, ascorbic acid, which is itself highly UV-C absorbing, does not exert a photoprotective action on the FX protein. As demonstrated, such an increase by an additive in UV-C absorbance can be easily compensated by the described absorbance-matching chemical dosimetry.

Example 8

Optimization of the Stirrer Type for Highly Absorbing Solutions

A highly-absorbing and viscous fibrinogen solution ($a_{253.7}$~13-14/cm, η~2 cp) was obtained by the dissolution of lyophilized fibrinogen concentrate (Fibrinogen TIM 3, Baxter BioScience). Both the corresponding model solution, and after spiking with bacteriophage Phi-X 174 lysate (1 mL lysate to 60 mL fibrinogen solution), 450 mL of such a fibrinogen solution were irradiated in the reactor described in Example 4 at 120 rpm with either a stacked impeller stirrer (three 3-blade impellers totally immersed, with a ~6 mm gap between the outer edge and the quartz glass cylinder) or a wiper stirrer (two 2-blade impellers at the bottom at the middle, and 2 axially parallel wiper blades at the outer edge, with a ~4 mm gap between the wiper and the quartz glass cylinder). 2 lamps were used. The bacteriophage titer was determined as described in Example 3.

| | stirrer type (120 rpm) | |
|---|---|---|
| | impeller | wiper |
| $a_{253.7}$ (1/cm) | 13.45 | 14.1 |
| viscosity (cp) | 2.0 | 2.1 |
| chemical dose rate (mJ/cm²)/min | 0.8398 | 0.8493 |
| Phi-X 174 inactivation rate k | −0.3121 | −0.3873 |

It is evident from the table in Example 8 that the wiper stirrer effects a better mixing at the moderate stirring speed of 120 rpm. The combination of chemical dosimetry and biodosimetry can thus be used to determine a dose distribution.

Example 9

Calibration of a Dosimeter Solution with an Lamp-Intensity- and Quantum Yield-Stabilized and Exposure Time-Controlled Calibration Device For reproducible and accurate exposure of a dosimeter solution in the thin-layer cuvette, a cuvette slot with a water-thermostated jacket was mounted onto the hinged back of a single lens reflex camera, and an aperture was milled into this back to expose the cuvette through the camera shutter. The camera's lens bayonet was mounted on the flange of a lamp housing containing a low-pressure mercury vapor lamp in a water-thermostated quartz glass jacket.

The lamp thermostating temperature was controlled with a externally circulating water thermostate to operate the lamp at its maximum UV-C output. The cuvette slot temperature was set within the range of the defined quantum yield of the iodide/iodate actinometer as given by Rahn (1997) and controlled with an externally circulating water cryostate. The camera shutter was set to 1 s exposure time and the shutter accuracy was determined using a photodiode connected to the microphone plug of a computer sound card. The shutter was found to maintain a constant exposure time of 1.000±0.002 s.

For the determination of the irradiance effective at the cuvette entrance window, the 0.6 M iodide/0.1 M iodate actinometer solution (Rahn 1997), which absorbs all incident photons completely, was filled into the 0.2 mm cuvette and exposed incrementally for 1, 2 and 3 s in the thermostated cuvette slot to ensure a constant quantum yield. Before the exposure, the spectrophotometer absorbance at 352 nm was set to zero, and after each exposure step, the absorbance increase was measured in the spectrophotometer at 352 nm. From the absorbance increase, the concentration of triiodide, from the temperature-dependent quantum yield, the number of incident photons, and from the photon energy and the cuvette cross-sectional area, the irradiance E was calculated. E (in mW/cm²) can thus be calculated from the absorbance increase Dabs at the exposure time t (in s), the cuvette surface A (in cm²) and the cuvette volume V (in L), the extinction coefficient E at the path length d (264.5 for 0.01 cm), the energy W/einstein at 253.7 nm=471528 J, and the quantum yield Φ=0.7545 at 21° C. (Rahn 1997), the according to the formula E=(Δabs×V×W×1000)/(E×A×Φ×t). So after 1 s exposure time, an absorbance increase of 0.0392 corresponded to an irradiance of 0.9262 mW/cm², after cumulative 2 s, the cumulative absorbance increase of 0.0781 corresponded to 0.9227 mW/cm², and after 3 s, a cumulative absorbance increase of 0.1170 corresponded to 0.9215 mW/cm². The average irradiance was 0.9235 mW/cm² with a standard deviation of 0.0020 mW/cm², demonstrating a very precise exposure for calibration by the electronically controlled shutter.

A dosimeter solution corresponding to an UV-C absorbance of $a_{253.7}$=6.5/cm and a viscosity of 1.16 cp was filled into a 0.2 mm cuvette and exposed in 3 s increments up to 75 s. After every exposure increment, the absorbance increase at 367 nm was read out with the unirradiated solution as the blank. The obtained calibration plot correlated with a second-order equation where the absorbance at 367 nm depends on the exposure fluence H.

| abs(367 nm, 0.2 mm) = A × H² + B × H + C | |
|---|---|
| coefficient | |
| A | −0.0000257179 |
| B | 0.0074523297 |
| C | 0.0006009852 |
| correlation | |
| R² | 0.999986 |

As seen in Example 9, the correlation $R^2$ close to unity indicates the precision of the calibration plot recorded by the means of an electronically controlled shutter. The second-order equation has the additional advantage that for an absorption value determined e.g. at the dose-rate measurement as described in Example 2, a plausible solution of this equation can be calculated easily. Calibration plots may also be segmented and such a second-order equation may be calculated for each segment to obtain a correlation $R^2$ as close to unity as possible.

Example 10

Determination of an Absorption-Dependent Radiometric Target Lamp Sum Dose of the 30 L Reactor by the Combined Use of Chemical Dosimetry and Radiometry to Ensure a Lamp-Failure Safe Robust Process The 30 L reactor described in Example 5 and equipped with 9 individually switchable lamps was validated with 10 different model dosimetric solutions and 4 lamps ($a_{253.7}$=3/cm to 12/cm in 1/cm increments, η=1.15 cp) to determine the dose rate (in (mJ/cm²)/min)), the lamp dose rate (in (mJ/cm²)/min)), and the irradiation time necessary for an effective dose of 20 mJ/cm². The lamp intensity was monitored with electronic radiometers and recorded with a chart recorder, and a sum counter was installed to sum up the signals from all radiometers during the irradiation. The lamp dose rate was determined as the radiometer sum signal increase with the irradiation time, and the lamp dose rate is orders of magnitudes higher than the chemical dose rate, because the radiometer sensors receive the UV light practically unattenuated by any absorbing medium. The irradiation time for a given target dose effective in the solution, e.g. 20 mJ/cm², is multiplied by the lamp dose rate to calculate the lamp sum dose as the irradiation parameter.

| Absorption coefficient $\alpha_{253.7}$ (1/cm) | Lamp sum dose $H_{lamp}$ for 20 mJ/cm² |
|---|---|
| 3 | 13393 |
| 4 | 18204 |
| 5 | 25230 |
| 6 | 29942 |
| 7 | 33770 |
| 8 | 38310 |
| 9 | 43704 |
| 10 | 48085 |
| 11 | 54620 |
| 12 | 60027 |

From the table it can be seen that the lamp sum dose correlates in a linear relation with the absorbance, expressed by the formula $H_{lamp}$=5058.9×$a_{253.7}$−1413 with a correlation $R^2$=0.9972 close to unity. The absorbance-dependent lamp sum dose, which itself is independent of any change in intensity, is therefore the ideal parameter for a robust irradiation process to ensure that the appropriate target dose has been applied. The irradiation process is controlled by the radiometric lamp sum dose in the way that upon attaining this pre-determined absorbance-dependent lamp sum dose, which is interpolated to every absorbance in the validation range, the lamps are turned off to terminate the irradiation.

Example 11

Simulation of Lamp Failure During the Lamp Sum Dose-Controlled Irradiation Process and Demonstration of the Correct Applied Target Dose Effective in the Solution A model solution ($a_{253.7}$=8/cm, η=1.15 cp) was irradiated in the 30 L reactor as described in Example 10. Two experiments were done in which after 10 min, one of the four lamps was switched off and either replaced by turning on a different lamp, or not by continuing and terminating the irradiation only with 3 lamps. The dose-rates were determined by chemical dosimetry, and upon attaining the lamp sum dose $H_{lamp}$=39058 mJ/cm² as calculated from the formula in the validation described in example 11, the lamps were turned off, and a sample was drawn to determine the dose effective in the solution.

In the first experiment with the replacement of the lamp after 10 min with another lamp, the lamp sum dose was reached after 16 min 43 s, and a dose of 19.7 mJ/cm² was measured in the model solution. In the second experiment without lamp replacement, the lamp sum dose was reached after 19 min 55 s, and a dose of 19.9 mJ/cm² was measured in the model solution.

From the effective doses measured after the irradiation time, which was required to attain the pre-determined lamp sum dose, it can be seen that the lamp sum dose-controlled process is even insensitive and robust against failure of a lamp during the irradiation process, because the lamp sum dose ensures the application of the correct effective dose.

REFERENCES

Adhikari C, Nurakami E G, Koutchma T, Beecham T: Chemical actinometry in UV treated juices, http://ift.confex.com/ift/2002/techprogram/papter_11210.htm accessed Dec. 16, 2003

Alfano O M, Romero R L, Cassano A E: Modeling of radiation transport and energy absorption in photoreactors. Advances in Transport Processes 4 (1986), 201-273.

Alfano O M, Romero R L, Cassano A E: Radiation field modeling in photoreactors-I. homogeneous media. Chemical Engineering Science 41 (1986), 3:421-444.

Allan W, Diffey B L: A device for minimizing the risk of overexposure of patients undergoing phototherapy. Photodermatology, Photophysiology and Photomedicine 18 (2002), 199-201

Aznar J A, Molina R, Montoro J M: Factor VIII/von Willebrand factor complex in methylene blue-treated fresh plasma. Transfusion 39 (1999), 7:748-750.

Barnett R N, Fox R A, Snavely J G: Hepatitis following the use of irradiated human plasma. Journal of the American Medical Association 144 (1950), 226-228

Battigelli D A, Sobsey M D, Lobe D C: The inactivation of hepatitis A virus and other model viruses by UV irradiation. Water Science and Technology 27 (1993), 3/4:339-342.

Battisto J R, Pringle R B, Nungester W J: The effect of UV irradiation on immune serum. Journal of Infectious Diseases 92 (1953), 85-88

Benesi E: Design of a centrifugal filmer for the ultraviolet irradiation of liquids. General Motors Engineering Journal 3 (1956), 2-8

Bering E, Meyer H: Methoden zur Messung der Wirksamkeit violetter and UV-Strahlenquellen (Methods for the measurement of the effectiveness of violet and ultraviolet radiation sources). Strahlentherapie 1 (1912), 189-207.

Bolton J R, Linden K G: Standardization of methods for fluence (UV dose) determination in bench-scale UV experiments. Journal of Environmental Engineering 129 (2003), 3: 209-215, Bolton J R: Ultraviolet principles and applications. EPA Newsletter 66 (1999), 9-36.

Bowen E J: The chemical aspects of light, $2^{nd}$ revised edition, Oxford: Clarendon Press 1949

Braslaysky S E, Houk K N, Verhoeven J W: Glossary of terms used in photochemistry. Pure and Applied Chemistry 68 (1996), 2223-2286.

Brauer H-D, Schmidt R: A new reusable chemical actinometer for UV irradiation in the 248-334 nm range. Photochemistry and Photobiology 37 (1983), 5:587-591.

Brown T T. Laboratory evaluation of selected disinfectants as virucidal agents against porcine parvovirus, pseudorabies virus, and transmissible gastroenteritis virus. American Journal of Veterinary Research 42 (1981), 6:1033-1036.

Budowsky E I, Kostyuk G V, Kost A A, Savin F A: Principles of selective inactivation of viral genome. II. Influence of stirring and optical density of the layer to be irradiated upon UV-induced inactivation of viruses. Archives of Virology 68 (1981), 3-4:249-256.

Cabaj A, Sommer R, Schoenen D: Biodosimetry: model calculations for UV water disinfection devices with regard to dose distribution. Water Research 30 (1996), 4:1003-1009.

Cabaj A, Sommer R: Measurement of ultraviolet radiation with biological dosemeters. Radiation Protection and Dosimetry 91 (2000) 1-3:139-142.

Calvert J G, Rechen H J L: Precision actinometry at low light intensities with malachite green leucocyanide. Journal of the American Chemical Society 74 (Apr. 20, 1952), 2101-2103.

Chin S, Jin R, Wang X-L, Hamman J, Marx G, Mou X, Andersson I, Lindquist L-O, Horowitz B: Virucidal treatment of blood protein products with UVC radiation. Photochemistry and Photobiology 65 (1997), 3:432-435.

Chin S, Williams B, Gottlieb P, Margolis-Nunno H, Ben-Hur E, Hamman J, Jin R, Dubovi E, Horowitz B: Virucidal short wavelength ultraviolet light treatment of plasma and factor VIII concentrate: protection of proteins by antioxidants. Blood 86 (1995), 11:4331-4336.

Claesson I M: The effect of ultraviolet light (I=2537 Å) on *Helix pomatia* hemocyanin and bovine serum albumin as studied by the changes in the ultraviolet spectrum and sedimentation behaviour. Arkiv för Kemi 10 (1956), 1:1-102

Cutler S S, Burbank B, and Marzullo E R: Hypocoagulability of certain irradiated plasmas. Journal of the American Medical Association 143 (1950), 1057-1059

Cutler S S, Burbank B, Farber E, Stern K G: Action of ultraviolet rays on fibrinogen. Plasma (Milano) 2 (1955), 285-295

Dainton F S, Sills S A: Use of nitrous oxide to discriminate between various forms of hydrogen atoms existing in aqueous solutions of potassium iodide irradiated with ultraviolet light. Nature 186 (Jun. 11, 1960):879

Di Benedetto C, Farhat N, Cioffi L A: Effetti delle radiazioni sul fibrinogeno. III. Elettroforesi su carta e tromboelastografia di fibrinogeno irradiato con U. V. (Radiation effects on fibrinogen. III. Paper electrophoresis and thromboelastography of UV-irradiated fibrinogen). Bolletino della Societa Italiana Biologica Sper 39 (1963), 2058-2061.

Di Benedetto C, Santamaria R, Cioffi L A: Effetti delle radiazioni sul fibrinogeno. V. Elettroforesi in fase libera e tromboelastografia di fibrinogeno irradiato con U. V. (Radiation effects on fibrinogen. V. Free-phase electrophoresis and thromboelastography of UV-irradiated fibrinogen). Bolletino della Societa Italiana Biologica Sper 39 (1963), 2064-2067.

Di Benedetto C, Santamaria R, Cioffi L A: Effetti delle radiazioni sul fibrinogeno. IV. Elettroforesi su gel di amido e tromboelastografia di fibrinogeno irradiato con U. V. (Radiation effects on fibrinogen. IV. Amide gel electrophoresis and thromboelastography of UV-irradiated fibrinogen). Bolletino della Societa Italiana Biologica Sper 39 (1963), 2061-2064.

Dichtelmüller H, Rudnick D, Breuer B, Gänshirt K H: Validation of virus inactivation and removal for the manufacturing procedure of two immunoglobulins and a 5% serum protein solution treated with beta-propiolactone. Biologicals 21 (1993), 3:259-268.

Dichtelmüller H, Stephan W, Prince A M, Gürtler L, Deinhardt F: Inactivation of HIV in plasma derivatives by beta-propiolactone and UV-irradiation. Infection 15 (1987), 5:367-369.

Dichtelmüller H, Stephan W: Kontrolle von Sterilisationsverfahren für Plasmaderivate mit Bakteriophagen. (Check of sterilization procedures for plasma derivatives by the use of bacteriophages). Immunität und Infektion 16 (1988), 1:18-20.

Engelhard H, Eikenberg K-R: Über die Einwirkung von ultraviolettem Licht auf Serum-Albumin. Zeitschrift für Naturforschung 10b (1955), 622-631

Erdmann K: Versuche zur Aufhebung der koagulierenden Wirkungen von ultraviolettem Licht und von Röntgenstrahlen auf Euglobulin mit Strahlen-Schutzstoffen (Experiments on the inhibition of the coagulating action of ultraviolet light and of x-rays on euglobulin by radiation-protecting substances). Protoplasma 45 (1956), 3:293-314.

Favaro G. Actinometry: concepts and experiments. In: Drugs: Photochemistry and Photostability, Special Publications of the Royal Society of Chemistry 225 (1998), 295-304.

Fisher G J, LeBlanc J C, Johns H E: A calorimetric determination of the quantum yield for the ionization of malachite green cyanide by ultraviolet radiation. Photochemistry and Photobiology 6 (1967), 757-767.

Forney L J and Pierson J A. Optimum photolysis in Taylor-Coiiette flow. American Institute of Chemical Engineers Journal 49 (2003) 3: 727-733

Frösner G G, Stephan W, Dichtelmüller H: Inactivation of hepatitis A virus added to pooled human plasma by beta-propiolactone treatment and ultraviolet irradiation. European Journal of Clinical Microbiology 2 (1983), 4:355-357.

Gauglitz G, Hubig S: Azobenzene as a convenient actinometer: evaluation values for UV mercury lines and for the $N_2$ laser lines. Journal of Photochemistry 15 (1981), 255-257.

Gauglitz G, Hubig S: Chemical actinometry in the UV by azobenzene in concentrated solution: a convenient method. Journal of Photochemistry 30 (1985), 121-125.

Gauglitz G, Hubig S: Photokinetische Grundlagen moderner chemischer Aktinometer (Photokinetic bases of modern chemical actinometers). Zeitschrift für Physikalische Chemie, Neue Folge 139 (1984), 237-246.

Gauglitz G. Modern chemical actinometry. EPA Newsletter (November 1983), 49-53.

Gelzhäuser P: Desinfektion von Trinkwasser durch UV-Bestrahlung (Disinfection of drinking water by UV-irradiation). Sindelfingen: Expert-Verlag, 1985.

Habel K, Sockrider B T: A continuous flow method of exposing antigens to ultraviolet radiation. Journal of Immunology 56 (1947), 273-279.

Hackradt A: Kolorimetrische Dosierung künstlicher Lichtquellen (Kromayersche Quarzlampe and Hohensonne) mittels des Autenried-Königsbergerschen Kolorimeters (Colorimetric dosimetry of artificial light sources (Kromayer's quartz lamp and sun tan lamp) by use of the Autenried-Königsberg colorimeter). Strahlentherapie 10 (1920), 1137-1144.

Hackradt A: Über die kolorimetrische Ausdosierung künstlicher Lichtquellen auf Grund der Zersetzung einer Jodwasserstofflösung (About the colorimetric dosimetry of artificial light sources based on the decomposition of aqueous hydrogen iodide). Strahlentherapie 12 (1922), 843-845.

Harris R E, Coleman P H, Morahan P S: Stability of Minute Virus of Mice to chemical and physical agents. Applied Microbiology 28 (1974), 3:351-354.

Hart H, Reid K, Hart W: Inactivation of viruses during ultraviolet light treatment of human intravenous immunoglobulin and albumin. Vox Sanguinis 64 (1993), 2:82-88.

Hartman F W, Kelly A R, LoGrippo G A: Four year study concerning the inactivation of viruses in blood and plasma. Gastroenterology 28 (1955), 244-256.

Havelaar A H, Nieuwstad T J, Meulemans C C E, van Olphen M; F-specific RNA bacteriophages as model viruses in UV disinfection of wastewater. Water Science and Technology 24 (1991), 2:347-352.

Heidt L J, Boyles H B: Influence of several variables encountered in photochemical work upon the intensity of wavelength 254 mµ produced by a quartz mercury vapor lamp of the low pressure type operating in water at 0-95° C. Journal of the American Chemical Society 73 (1951):5728-5731

Heinrich D, Kotitschke R, Berthold H: Clinical evaluation of the hepatitis safety of a beta-propiolactone/ultraviolet treated factor IX concentrate (PPSB). Thrombosis Research 28 (1982), 1:75-83.

Heinrich D, Sugg U, Brackmann H H, Stephan W, Lissner R: Virus safety of beta-propiolactone treated plasma preparations: clinical experiences. Development in Biological Standardization 67 (1987), 311-317.

Hellbrugge T F, Marx R: Elektrophoretische und gerinnungsphysiologische Untersuchungen an UV-bestrahltem Plasma und Plasmafraktionen (electrophoretic and coagulation physiological investigations on UV irradiated plasma and plasma fractions). Medizinische Monatsschrift 6 (1952), 1: 30-36

Henzler H-J, Kaiser K. Avoiding viral contamination in biotechnological and pharmaceutical processes. Nature Biotechnology 16 (1998), 11: 1077-1079

Ijichi K, Hammerle O A, Lineweaver H, Kline L: Effect of ultraviolet irradiation of egg liquids on *Salmonella* destruction and performance quality with emphasis on egg white, Food Technol. 18 (1964), 124 (1628)-128 (1632)

James G, Korns R F, Wright A W: Homologous serum jaundice associated with the use of irradiated human plasma. Journal of the American Medical Association 144 (1950), 228-230

Kallenbach N R, Cornelius P A, Negus D, Montgomerie D, Englander S: Inactivation of viruses by ultraviolet light. In: Morgenthaler J-J. (ed.): Virus inactivation in plasma products, Current Studies in Hematology and Blood Transfusion 56 (1989), 70-82.

Kirk A D, Namasivayam C: Errors in ferrioxalate actinometry. Analytical Chemistry 55 (1983), 2428-2429.

Kleczkowski A, Gold A H: Effects of ultraviolet radiation on antigenicity of horse serum albumin: formation of new determinants. Photochemistry and Photobiology 1 (1962), 299-304

Kleczkowski A: Inactivation of antibodies by ultraviolet radiation. British Journal of Experimental Pathology 35 (1954), 402-413

Kleim J-P, Bailly E, Schneweis K E, Brackmann H H, Hammerstein U, van Loo B, Oldenburg J: Acute HIV-1 infection in patients with hemophilia B treated with beta-propiolactone-UV-inactivated clotting factor. Thrombosis and Haemostasis 64 (1990), 2:336-337.

Koutchma T, Adhikari C: Effectiveness of the UV disinfection of juice. IUVA News 4 (2002), 5: 21-23.

Kryschi R, Gürtler K R, Perkampus H-H: Photochemische Bestimmung der Strahlungsleistung von UV-Strahlern für die Wasserdesinfektion (Photochemical determination of the UV-sources' radiant power for water disinfection). Vom Wasser 70 (1988), 197-207.

Kuhn H J, Braslaysky S E, Schmidt R: Chemical actinometry. Pure & Applied Chemistry 61 (1989) 2:187-210.

Kupfer B, Oldenburg J, Brackmann H H, Matz B, Schneweis K E, and Kaiser R: Beta-propiolactone UV inactivated clotting factor concentrate is the source of HIV-infection of 8 hemophilia B patients: confirmed. Thrombosis and Haemostasis 74 (1995), 5:1386-1387.

Kurth J, Waldmann R, Heith J, Mausbach K, Burian R: Efficient inactivation of viruses and mycoplasma in animal sera using UVC irradiation. In: Brown F, Cartwright T, Horaud F, Spieser J M (eds.): Animal sera, animal sera derivatives and substitutes used in the manufacture of pharmaceuticals: viral safety and regulatory aspects, Development in Biological Standardization (Karger, Basel) 99 (1999), 111-118.

Lankford K V, Mosunjac M, Hillyer C D: Effects of UVB irradiation on cytokine generation, cell adhesion molecules, and cell activation markers in T-lymphocytes and peripheral blood HPCs. Transfusion 40 (2000), 3:361-367.

Larin N M: Effect of ultraviolet irradiation on electrophoretic properties of serum protein. Nature 181 (4601 (Jan. 4, 1958)): 65

Latarjet R, Wahl R: Précisions sur l'inactivation des Bactériophages par les rayons ultraviolets (Details about the inactivation of bacteriophages by ultraviolet rays). Annales de l'Institut Pasteur 71 (1945), 336-339.

Latarjet R., Morenne P, Berger R: Un appareil simple pour le dosage des rayonnements ultraviolets emis par les lampes germicides (A simple apparatus for the dosage of ultraviolet radiation emitted by germicidal lamps). Annales del'Institut Pasteur 85 (1953), 174-184

Launer H F, Hammerle O A: UV dosage measurement in a geometrically complex system with light-sensitive paper. Quantum yield for *Salmonella* kill in egg white. Photochemistry and Photobiology 4 (1965), 2: 265-267

Mark G, Schuchmann M N, Schuchmann H P, von Sonntag C: The photolysis of potassium peroxodisulphate in aqueous solution in the presence of tert-butanol: a simple actinometer for 254 nm radiation. Journal of Photochemistry and Photobiology A: Chemistry 55 (1990), 157-168.

Martin C J, Pye S D: A study of the directional response of ultraviolet radiometers: II. Implications for ultraviolet phototherapy derived from computer simulations. Physics in Medicine and Biology 45 (2000), 9:2713-2729

Marx G, Miou X, Freed R, Ben-Hur E, Yang C, Horowitz B: Protecting fibrinogen with rutin during UVC irradiation for viral inactivation. Photochemistry and Photobiology 63 (1996), 4:541-546.

McCall K B, Gordon F H, Bloom F C, Hyndman L A, Taylor H L, Anderson H D: Methods for the preparation and ultraviolet irradiation of human fibrinogen for intravenous use. Journal of the American Pharmaceutical Association, Scientific Edition 46 (1957), 5:295-298.

McLean I W Jr., Taylor A R: Experiences in the production of poliovirus vaccines. Progress in Medical Virology 1 (1958), 122-164

Milzer A, Oppenheimer F, Levinson S O: A new method for the production of potent inactivated vaccines with ultraviolet irradiation. Journal of Immunology 50 (1945), 331-340.

Moroson H, Gregoriades A: A sensitive chemical actinometer for ultraviolet radiation. Nature 204 (Nov. 14, 1964) 676-678.

Morowitz H J: Absorption effects in volume irradiation of microorganisms. Science 111 (1950), 229-230.

Murray R, Oliphant J W, Tripp J T, Hampil B, Ratner F, Diefenbach W C L, Geller H: Effect of ultraviolet radiation on the infectivity of icterogenic plasma. Journal of the American Medical Association 157 (1955), 1:8-14

Neefe J R: Viral hepatitis: problems and progress. Annals of Internal Medicine 31 (1949), 857-870

Oliphant J W, Hollaender A: Homologous serum jaundice: experimental inactivation of etiologic agent in serum by ultraviolet irradiation. Public Health Reports 61 (1946), 17:598-602.

Oppenheimer F, Benesi E, Taylor A R: The ultraviolet irradiation of biological fluids in thin-flowing films. American Journal of Public Health 49 (1959), 7:903-923.

Pamphilon D H: The treatment of blood components with ultraviolet-B irradiation. Vox Sanguinis 74 (Suppl. 2) (1998), 15-19.

Prince A M, Stephan W, Brotman B. Inactivation of non-A, non B virus infectivity by a beta-propiolactone/ultraviolet irradiation treatment and aerosil adsorption procedure used for preparation of a stabilized human serum. Vox Sanguinis 46 (1984): 2:80-85.

Prince A M, Stephan W, Brotman B: Beta-propiolactone/ultraviolet irradiation: a review of its effectiveness for inactivation of viruses in blood derivatives. Reviews of infectious diseases 5 (1983), 1:92-106.

Proctor W R, Cook J S, Tennant R W: Ultraviolet photobiology of Kilham rat virus and the absolute ultraviolet photosensitivities of other animal viruses: influence of DNA strandedness, molecular weight, and host cell repair. Virology 49 (1972) 368-378.

Prodouz K N, Fratatoni J C, Boone E J, Bonner J F: Use of laser-UV for inactivation of virus in blood products. Blood 70 (1987), 2:589-592.

Pustoslemsek P, Kloft M, Kotitschke R: Biotest-Stellungnahme zur HIV-1-Serokonversion von 1990 an elf Patienten, die mit beta-Propiolacton/UV virusinaktiviertem PPSB behandelt wurden (Biotest statement to the HIV-1 seroconversion of 11 patients in 1990, who were treated with beta-propiolactone/UV-inactivated PPSB). Infusionstherapie and Transfusionsmedizin 20 (1993), 6:344-346.

Pye S D, Martin C J: A study of the directional response of ultraviolet radiometers: I. Practical evaluation and implication for ultraviolet measurement standards. Physics in Medicine and Biology 45 (2000), 9:2701-2712

Qualls R G, Johnson J D: Bioassay and dose measurement in UV disinfection. Applied and Environmental Microbiology 45 (1983), 3:872-877.

Rahn R O, Stefan M I, Bolton J R, Goren E, Shaw P-S, Lykke K R: Quantum yield of the iodide/iodate chemical actinometer: dependence on wavelength and concentration. Photochemistry and Photobiology 78 (2003), 2:146-152

Rahn R O, Xu P, Miller S L: Dosimetry of room-air germicidal (254 nm) radiation using spherical actinometry. Photochemistry and Photobiology 70 (1999), 3:314-318

Rahn R O: Potassium iodide as a chemical actinometer for 254 nm radiation: use of iodate as an electron scavenger. Photochemistry and Photobiology 66 (1997), 4:450-455

Rahn R O: Use of potassium iodide as a chemical actinometer. Photochemistry and Photobiology 58 (1993), 6:874-880

Rideal E K, Roberts R: The photochemistry of native proteins. Proceedings of the Royal Society A 205 (1951), 391-408

Rommelaere J, Vos J M, Cornelis J J, Ward D C: UV-enhanced reactivation of minute-virus-of-mice: stimulation of a late step in the viral life cycle. Photochemistry and Photobiology 33 (1981), 6:845-854.

Schenck H J, Simak P, Haedicke E: Structure of polyvinylpyrrolidone-iodine (povidone-iodine). Journal of Pharmaceutical Science 68 (1979), 12:1505-1509.

Schulz C R, Cervantes P, and Laplace C: Development of a flow-through actinometry monitor for dose measurements in UV disinfection reactors. Conference Prooceedings (on CD-ROM) of the International Ultraviolet Association's $1^{st}$ International Congress on Ultraviolet Technologies, Washington DC, Jun. 15-16, 2001.

Sczechowskii J G, Koval C A, Noble R D: A Taylor vortex reactor for heterogeneous photocatalysis. Chemical Engineering Science 50 (1995), 20: 3163-3173

Setlow R and Boyce R. The ultraviolet light inactivation of Phi-X 174 bacteriophage at different wave lengths and pHs. Biophysical Journal 1 (September 1960), 29-41.

Smolens J, Stokes J. Combined use of ultraviolet irradiation and beta-propiolactone sterilization of serums infected with a virus. Proceedings of the Society of Experimental Biology and Medicine 86 (1954), 538-539.

Sommer R, Pribil W, Appelt S, Gehringer P, Eschweiler H, Leth H, Cabaj A, Haider T: Inactivation of bacteriophages in water by means of non-ionizing (UV-253.7 nm) and ionizing (gamma) radiation: a comparative approach. Water Research 35 (2001), 13:3109-3116.

Stephan W, Kotitschke R, Prince A M, Brotman B: Long-term tolerance and recovery of beta-propiolactone/ultraviolet (β-PL/UV) treated PPSB in chimpanzees. Thrombosis und Haemostasis (Stuttgart) 46 (1981), 2:511-514.

Stephan W. Fractionation of cold-sterilized plasma. A new concept in production of non-infectious plasma proteins. Arzneimittel-Forschung/Drug Research 32 (II) (1982), 8:799-801.

Stephan W: Activity and storage stability of proteins in a hepatitis-free human serum preparation. Arzneimittel-Forschung/Drug Research 32 (II) (1982), 8:802-806.

Stephan W: Inactivation of hepatitis viruses and HIV in plasma and plasma derivatives by treatment with beta-propiolactone/UV irradiation, in: Morgenthaler J-J. (ed.): Virus inactivation in plasma products, Current Studies in Hematology and Blood Transfusion 56 (1989), 122-127.

Suhrmann R, Kollath W: Quantitative Messungen im sichtbaren und ultravioletten Absorptionsspektrum des Blutes und seiner Bestandteile. Zweiter Teil: Plasma und Serum (Quantitative measurements in the visible and ultraviolet absorption spectrum of blood and ist components. Part two: plasma and serum). Strahlentherapie 27 (1928), 572-586.

Taylor A R, Kay W W, McLean I W Jr., Oppenheimer F, Stimpert F D: Effect of ultraviolet light on poliomyelitis virus. Journal of Immunology 78 (1957), 45-55

Taylor A R, Kay W W, Timm E A, Hook A E, and McLean I W Jr. Inactivation of poliomyelitis virus for the preparation of vaccines. I. Formalin and ultraviolet irradiation. Journal of Immunology 79 (1957), 265-275

Taylor A R, Sharp D G, Beard D, Finkelstein H, Beard J W. Influence of ultraviolet light on equine encephalomyelitis virus proten (eastern strain). Journal of Infectious Diseases 69 (1941), 224-231

Taylor A R: Effects of nonionizing radiations on animal viruses. Annals of the New York Academy of Sciences 83 (Jan. 13, 1960), 670-683

Taylor D K, Anstey A V, Coleman A J, Diffey B L, Farr P M, Ferguson J, Ibbotson S, Langmack K, Lloyd J J, McCann P, Martin C J, Menage H D P, Moseley H, Murphy G, Pye S D, Rhodes L E, Rogers S: Guidelines for dosimetry and calibration in ultraviolet radiation therapy: a report of a British Photodermatology Group workshop. British Journal of Dermatology 146 (2002) 5:755-763

Ternovoi K S, Bondar W, Butylin Y P, Kondratenko P A, Kurik M V, Sakun Y M: (An actinometric method for comparing the parameters of equipment for the ultraviolet irradiation of the blood). Meditsinkaia Tekhnika 4 (1988), 16-19.

Vincze L, Kemp T J, Unwin P R: Flow actinometry in a thin-film reactor: modeling, and measurements. Journal of Photochemistry and Photobiology A: Chemistry 123 (1999), 7-13.

von Sonntag J: The influence of solute absorbance in laser flash photolysis-actinometry in experiment and theory at non-vanishing absorbance. Journal of Photochemistry and Photobiology A: Chemistry 126 (1999), 1-5.

Wright H B and Sakamoto G: UV Dose required to achieve incremental log inactivation of bacteria, viruses, and protozoa. Trojan Technologies, London ON/Canada, 2001. Document accessible at the IUVA members' internet website: http://www.iuva.org/MemberZone/Downloads/UV%20Dose%20Table%20Rev%20Sept[1].%2012%202001.doc Yokota T, Suzuki S: Estimation of light absorption rate in a tank type photoreactor with multiple lamps inside, Journal of Chemical Engineering of Japan, 28 (1995), 3: 300-305

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

All references cited herein, including all publications, and all U.S. and foreign patents and patent applications are specifically and entirely incorporated herein by reference. It is intended that the specification and examples be considered exemplary only, with the true scope and spirit of the invention indicated by the following claims.

The invention claimed is:

1. A method for inactivating microorganisms in a biological fluid, the method comprising:
   (a) determining a target light fluence effective to inactivate microorganisms in the biological fluid by:
      (i) irradiating a dosimetric solution for calibration with a known incident light fluence of light comprising a first wavelength in a layer of the dosimetric solution having an optical path-length sufficiently thin to absorb less than 80% of the incident light comprising the first wavelength, thereby effecting a chemical change in the dosimetric solution measurable by a change in absorbance of the dosimetric solution at a second wavelength,
      wherein the dosimetric solution matches the absorption coefficient of the biological fluid at the first wavelength, and further wherein the dosimetric solution is not a sample of the biologic fluid,
      (ii) measuring the change in absorbance of the dosimetric solution at the second wavelength,
      (iii) correlating the change in absorbance of the dosimetric solution to the known incident light fluence applied to the dosimetric solution to determine an effective light fluence applied to the dosimetric solution, and
      (iv) correlating the effective light fluence applied to the dosimetric solution to a target light fluence effective to inactivate microorganisms in the biological fluid to determine the target light fluence effective to inactivate microorganisms in the biological fluid upon irradiation in a photoinactivation reactor; and
   (b) irradiating the biological fluid in the photoinactivation reactor with the target light fluence of the light comprising the first wavelength.

2. The method according to claim 1, wherein the optical path length of the dosimetric solution is sufficiently thin to absorb 50% or less of the incident light comprising the first wavelength.

3. The method according to claim 1, further comprising monitoring the intensity of the one or more light sources during the irradiating (b) in order to determine a cumulative lamp intensity signal corresponding to the target light fluence applied to the biological fluid.

4. The method according to claim 1, wherein the first wavelength of the light is in the UV range.

5. The method according to claim 1, wherein the dosimetric solution comprises an agent or a combination of agents selected from the group consisting of alkali metal, alkaline earth metal and ammonium iodide, aqueous uridine phosphate, alkali metal, alkaline earth metal and ammonium salts of benzoic acid, and alkali metal, alkaline earth metal and ammonium peroxodisulfate, tert-butanol, and polyvinylpyrrolidone.

6. The method according to claim 1, wherein the dosimetric solution comprises potassium iodide and potassium iodate.

7. The method according to claim 1, wherein the dosimetric solution comprises potassium iodide, potassium iodate, and polyvinylpyrrolidone.

8. The method according to claim 1, wherein the dosimetric solution comprises sodium benzoate.

9. The method according to claim 1, wherein the dosimetric solution comprises a diluted potassium peroxodisulfate/tert-butanol actinometer.

10. The method according to claim 1, wherein the biological fluid is contained in a stirred-batch photoinactivation reactor.

11. The method according to claim 1, wherein said biological fluid comprises at least one additive to reduce damage and loss of biological activity of said fluid.

12. The method according to claim 1, wherein said method is performed in conjunction with at least one other sterilization or microorganism inactivation method.

13. The method according to claim 1, wherein said method is performed in conjunction with a solvent detergent treatment.

14. The method of claim 1, wherein the dosimetric solution matches the absorption coefficient of the biological fluid at the first wavelength and the viscosity of the biological fluid.

15. The method of claim 1, wherein the light comprising a first wavelength is a polychromatic light.

16. The method of claim 1, wherein the target light fluence effective to inactivate microorganisms in the biological fluid is determined by biodosimetry.

17. A method for determining a target light fluence effective to inactivate microorganisms in a biological fluid, the method comprising:
   (a) irradiating a dosimetric solution for calibration with a known incident light fluence of light comprising a first wavelength in a layer of the dosimetric solution having an optical path-length sufficiently thin to absorb less than 80% of the incident light comprising the first wavelength, thereby effecting a chemical change in the dosimetric solution measurable by a change in absorbance of the dosimetric solution at a second wavelength,
   wherein the dosimetric solution matches the absorption coefficient of the biological fluid at the first wavelength, and further wherein the dosimetric solution is not a sample of the biologic fluid,
   (b) measuring the change in absorbance of the dosimetric solution at the second wavelength,
   (c) correlating the change in absorbance of the dosimetric solution to the known incident light fluence applied to the dosimetric solution to determine an effective light fluence applied to the dosimetric solution, and
   (d) correlating the effective light fluence applied to the dosimetric solution to a target light fluence effective to inactivate microorganisms in the biological fluid to determine the target light fluence effective to inactivate microorganisms in the biological fluid upon irradiation in a photoinactivation reactor.

18. The method according to claim 17, wherein the optical path length of the dosimetric solution is sufficiently thin to absorb 50% or less of the incident light comprising the first wavelength.

19. The method according to claim 17, further comprising monitoring the intensity of the one or more light sources during the irradiating (b) in order to determine a cumulative lamp intensity signal corresponding to the target light fluence applied to the biological fluid.

20. The method according to claim 17, wherein the first wavelength of the light is in the UV range.

21. The method according to claim 17, wherein the dosimetric solution comprises an agent or a combination of agents selected from the group consisting of alkali metal, alkaline earth metal and ammonium iodide, aqueous uridine phosphate, alkali metal, alkaline earth metal and ammonium salts of benzoic acid, and alkali metal, alkaline earth metal and ammonium peroxodisulfate, tert-butanol, and polyvinylpyrrolidone.

22. The method according to claim 17, wherein the dosimetric solution comprises a diluted potassium iodide and potassium iodate.

23. The method according to claim 17, wherein the dosimetric solution comprises potassium iodide, potassium iodate, and polyvinylpyrrolidone.

24. The method according to claim 17, wherein the dosimetric solution comprises sodium benzoate.

25. The method according to claim 17, wherein the dosimetric solution comprises potassium peroxodisulfate and tert-butanol.

26. The method according to claim 17, wherein said method is performed in conjunction with at least one other sterilization or microorganism inactivation method.

27. The method according to claim 17, wherein said method is performed in conjunction with a solvent detergent treatment.

28. The method of claim 17, wherein the dosimetric solution matches the absorption coefficient of the biological fluid at the first wavelength and the viscosity of the biological solution.

29. The method of claim 17, wherein the light comprising a first wavelength is a polychromatic light.

30. The method of claim 17, wherein the target light fluence effective to inactivate microorganisms in the biological fluid is determined by biodosimetry.

* * * * *

UNITED STATES PATENT AND TRADEMARK OFFICE
CERTIFICATE OF CORRECTION

PATENT NO. : 8,986,607 B2
APPLICATION NO. : 10/547172
DATED : March 24, 2015
INVENTOR(S) : Anderle et al.

Page 1 of 1

It is certified that error appears in the above-identified patent and that said Letters Patent is hereby corrected as shown below:

In the Claims:

Column 40, Claim 22, line 20: please delete "a diluted"

Signed and Sealed this
Eleventh Day of August, 2015

Michelle K. Lee
*Director of the United States Patent and Trademark Office*